United States Patent
Nayak et al.

(10) Patent No.: US 12,125,604 B2
(45) Date of Patent: Oct. 22, 2024

(54) PRE-PATIENT COLLIMATOR HAVING A BUILT-IN ALIGNMENT MECHANISM

(71) Applicant: GE PRECISION HEALTHCARE LLC, Wauwatosa, WI (US)

(72) Inventors: Vishwanath Nayak, Bangalore (IN); Saiesh Suryakant Raiker, Margao (IN); Sanjay Dyavaiah Patil, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 316 days.

(21) Appl. No.: 17/591,143

(22) Filed: Feb. 2, 2022

(65) Prior Publication Data
US 2023/0245795 A1   Aug. 3, 2023

(51) Int. Cl.
G21K 1/04 (2006.01)
A61B 6/03 (2006.01)
A61B 6/06 (2006.01)

(52) U.S. Cl.
CPC .............. G21K 1/04 (2013.01); *A61B 6/035* (2013.01); *A61B 6/06* (2013.01)

(58) Field of Classification Search
CPC .................................. G21K 1/04; G21K 1/10
See application file for complete search history.

(56) References Cited

U.S. PATENT DOCUMENTS

| | | | |
|---|---|---|---|
| 7,254,216 B2 * | 8/2007 | Thandiackal ......... | A61B 6/032 378/158 |
| 7,634,047 B2 * | 12/2009 | Popescu .............. | A61B 6/4028 378/19 |
| 2005/0031084 A1 * | 2/2005 | Toth .................... | A61B 6/4035 378/156 |
| 2007/0025520 A1 * | 2/2007 | Thandiackal ........... | G21K 1/10 378/157 |

(Continued)

FOREIGN PATENT DOCUMENTS

| CN | 202960556 U | 6/2013 |
|---|---|---|
| JP | 6298300 A | 5/1987 |

(Continued)

OTHER PUBLICATIONS

EP application 23152673.2 filed Jan. 20, 2023—extended Search Report issued Oct. 24, 2023; 14 pages.

(Continued)

*Primary Examiner* — Dani Fox
*Assistant Examiner* — Soorena Kefayati
(74) *Attorney, Agent, or Firm* — Fletcher Yoder P.C.

(57) ABSTRACT

A pre-patient collimator for a CT imaging system is provided. The pre-patient collimator includes a collimator housing including a plurality of walls, wherein the plurality of walls includes a first wall configured to face an X-ray source when the pre-patient collimator is coupled to the CT imaging system and a second wall and a third wall flanking the first wall. The pre-patient collimator also includes a bowtie filter assembly disposed within the collimator housing and includ- (Continued)

ing a bowtie filter. The pre-patient collimator further includes an adjustment mechanism configured to move the bowtie filter assembly in a lateral direction between the second wall and the third wall within the collimator housing.

18 Claims, 24 Drawing Sheets

(56) References Cited

U.S. PATENT DOCUMENTS

| | | | | |
|---|---|---|---|---|
| 2011/0249787 | A1* | 10/2011 | Frey | A61B 6/06 378/62 |
| 2013/0156163 | A1* | 6/2013 | Liu | G06T 11/005 378/207 |
| 2014/0112441 | A1* | 4/2014 | Becker | A61B 6/545 378/62 |
| 2014/0140471 | A1* | 5/2014 | Tybinkowski | G21K 1/02 378/19 |
| 2014/0192950 | A1* | 7/2014 | Pelc | A61B 6/405 378/4 |
| 2014/0294141 | A1* | 10/2014 | Hsieh | G21K 1/10 378/19 |
| 2015/0302946 | A1* | 10/2015 | Ofer | G21K 1/043 378/160 |
| 2015/0305698 | A1* | 10/2015 | Katchalski | A61B 6/4035 378/19 |
| 2015/0313569 | A1* | 11/2015 | Stevens | A61B 6/544 378/8 |
| 2016/0113602 | A1* | 4/2016 | Wang | A61B 6/583 378/158 |
| 2017/0150940 | A1* | 6/2017 | Lou | A61B 6/032 |
| 2018/0310899 | A1* | 11/2018 | Garlow | A61B 6/5205 |
| 2019/0336086 | A1* | 11/2019 | Proksa | A61B 6/4035 |
| 2020/0051708 | A1* | 2/2020 | Smith | G21K 1/04 |
| 2020/0105432 | A1* | 4/2020 | Sharpless | A61N 5/1045 |
| 2020/0330065 | A1 | 10/2020 | Zhan | |
| 2021/0020325 | A1* | 1/2021 | Yan | G21K 1/10 |
| 2021/0059633 | A1* | 3/2021 | Levinson | A61B 6/488 |

FOREIGN PATENT DOCUMENTS

| | | |
|---|---|---|
| JP | 2006346274 A | 12/2006 |
| JP | 2020175169 A | 10/2020 |
| WO | 2009096361 A1 | 8/2009 |

OTHER PUBLICATIONS

JP patent application 2023-004812 filed Jan. 17, 2023—Office Action issued Feb. 21, 2024; 6 pages; Machine Translation.

JP2006346274 English Abstract; Espacenet search May 21, 2024; 1 page.

WO2009096361 English Abstract; Espacenet search May 21, 2024; 1 page.

* cited by examiner

PRE-PATIENT COLLIMATOR HAVING A BUILT-IN ALIGNMENT MECHANISM

BACKGROUND

The subject matter disclosed herein relates to medical imaging systems and, more particularly, to a pre-patient collimator having additively manufactured components.

In computed tomography (CT), X-ray radiation spans a subject of interest, such as a human patient, and a portion of the radiation impacts a detector where the image data is collected. In digital X-ray systems a photodetector produces signals representative of the amount or intensity of radiation impacting discrete pixel regions of a detector surface. The signals may then be processed to generate an image that may be displayed for review. In the images produced by such systems, it may be possible to identify and examine the internal structures and organs within a patient's body. In CT systems a detector array, including a series of detector elements or sensors, produces similar signals through various positions as a gantry is displaced around a patient, allowing volumetric reconstructions to be obtained.

A CT imaging system may include a pre-patient collimator to ensure the subject of interest receives the intended dose. The collimator blades of the pre-patient collimator are adjusted in front of the X-ray source to create an appropriate opening or aperture to transmit X-rays for the scan as set by the operator. Adjustment of the pre-patient collimator is key to obtaining a precisely shaped X-ray beam for obtaining a high quality image of a patient. Typically, during system alignment, the X-ray filter (e.g., bowtie filter) has to be adjusted to center it with the X-ray beam. This involves either having to move the entire collimator (which is typically very heavy) or by removing multiple components (e.g., covers) of the collimator to move the X-ray filter. In certain cases, during the system alignment (e.g., during an air scan), the X-filter needs to be removed. This makes the procedure tedious and time consuming.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In one embodiment, a pre-patient collimator for a CT imaging system is provided. The pre-patient collimator includes a collimator housing including a plurality of walls, wherein the plurality of walls includes a first wall configured to face an X-ray source when the pre-patient collimator is coupled to the CT imaging system and a second wall and a third wall flanking the first wall. The pre-patient collimator also includes a bowtie filter assembly disposed within the collimator housing and including a bowtie filter. The pre-patient collimator further includes an adjustment mechanism configured to move the bowtie filter assembly in a lateral direction between the second wall and the third wall within the collimator housing.

In another embodiment, a pre-patient collimator for a CT imaging system is provided. The pre-patient collimator includes a collimator housing. The pre-patient collimator also includes a bowtie filter assembly disposed within the collimator housing and including a bowtie filter. The pre-patient collimator further includes an adjustment mechanism configured to move the bowtie filter assembly in a first direction and a second direction within the collimator housing, wherein movement of the bowtie filter assembly in the first direction is independent of movement of the bowtie filter assembly in the second direction, and wherein the first direction and the second direction are orthogonal to each other.

In a further embodiment, a method for performing collimator bowtie filter centering. The method includes obtaining, at a processor, air scan data acquired via an air scan utilizing a computed tomography (CT) imaging system with a bowtie filter moved out of view of an X-ray beam emitted by an X-ray source of the CT imaging system prior to an air scan to obtain the air scan data, wherein the bowtie filter is disposed within a bowtie filter assembly disposed within a collimator housing, and wherein the bowtie filter assembly is configured to be moved in a first direction and a second direction within the collimator housing, the first direction being orthogonal to the second direction. The method also includes obtaining, at the processor, alignment data acquired via an air scan utilizing the CT imaging system with the bowtie filter moved in the second direction to within the scan plane prior to an alignment scan to obtain the air scan data. The method further includes calculating, via the processor, an offset distance of the bowtie filter from a beam line path of the X-ray beam. The method still further includes comparing, via the processor, the offset distance to an acceptable range for a desired center position of the bowtie filter within the X-ray beam. The method yet further includes calculating, via the processor, a distance to move the bowtie filter in the second direction to center the bowtie filter within the X-ray beam when the offset distance is outside the acceptable range. The method even further includes moving, in response to a control signal from the processor, the bowtie filter in the second direction by the distance.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
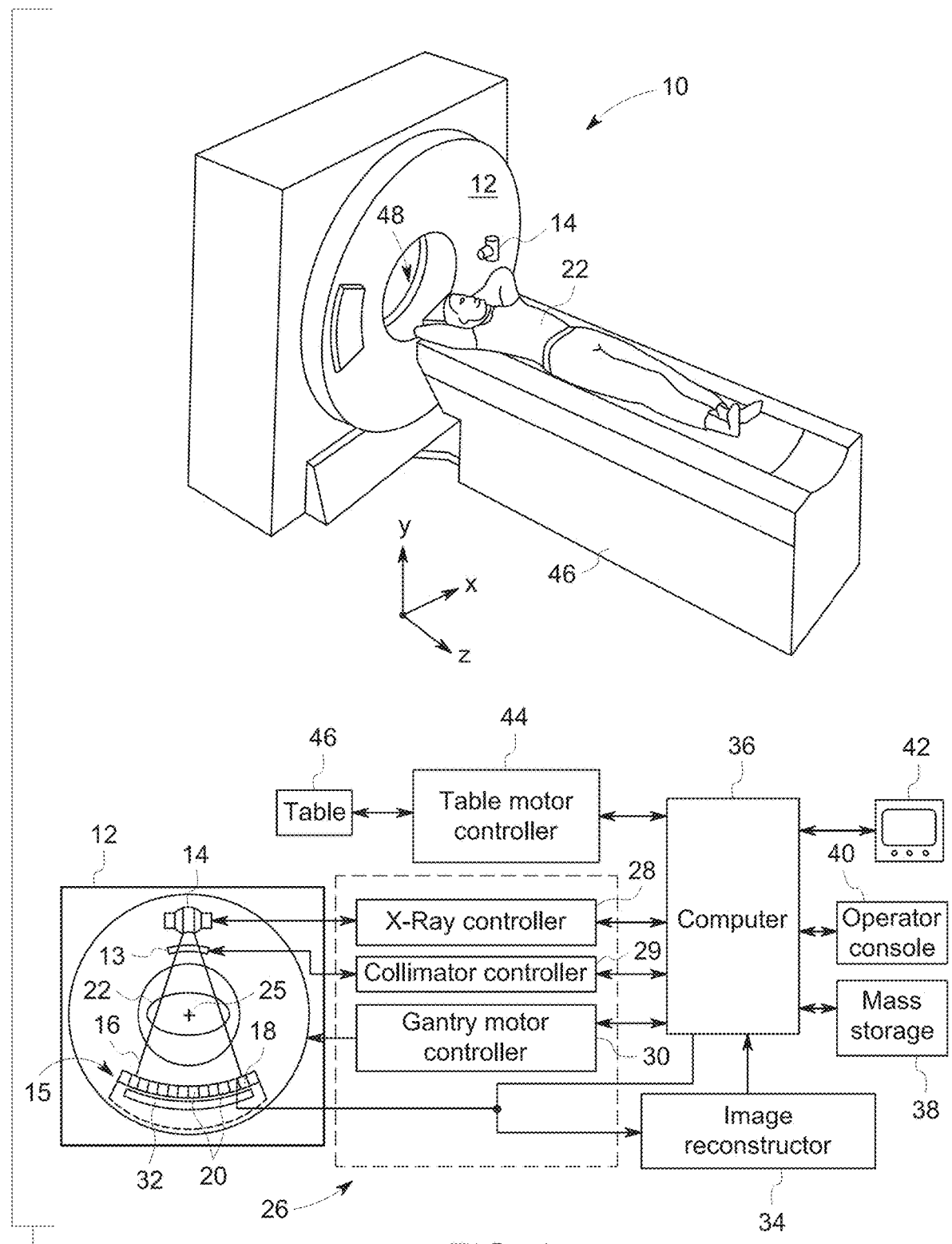
FIG. 1 is a combined pictorial view and block diagram of a computed tomography (CT) imaging system as discussed herein.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion may be provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as tomographic image reconstruction for industrial Computed Tomography (CT) used in non-destructive inspection of manufactured parts or goods (i.e., quality control or quality review applications), and/or the non-invasive inspection of packages, boxes, luggage, and so forth (i.e., security or screening applications). In general, the present approaches may be useful in any imaging or screening context or image processing field utilizing a collimator to control a size of X-ray beams.

The present disclosure provides an in-built alignment mechanism disposed within a pre-patient collimator (e.g., additively manufactured pre-patient collimator) for precise and easy adjustments of the collimator (e.g., adjustment of a bowtie filter integrated with the pre-patient collimator) during system alignment. In particular, the in-built alignment mechanism enables a bowtie filter to be adjusted (e.g., to be centered with respect to an X-ray beam path to provide very good image quality) in a both a lateral direction and a transverse direction independent of each other. The configuration of the in-built alignment mechanism also enables adjustments (e.g., via an actuator mechanism) of the bowtie filer to occur from outside a collimator housing without having to remove or disassemble a subcomponent (e.g., bowtie filter) from the collimator during the system alignment. In addition, the in-built alignment mechanism is configured to be utilized with different types of bowtie filters and is scalable to be utilized with different imaging platforms.

With the preceding in mind and referring to FIG. 1, a CT imaging system 10 is shown, by way of example. The CT imaging system includes a gantry 12. The gantry 12 has an X-ray source 14 that projects a beam of X-rays 16 toward a detector assembly 15 on the opposite side of the gantry 12. The X-ray source 14 projects the beam of X-rays 16 through a pre-patient collimator or collimator assembly 13 that determines the size of the beam of X-rays 16. The detector assembly 15 includes a collimator assembly 18 (post-patient collimator assembly), a plurality of detector modules 20 (e.g., detector elements or sensors), and data acquisition systems (DAS) 32. The plurality of detector modules 20 detect the projected X-rays that pass through a patient 22, and DAS 32 converts the data to digital signals for subsequent processing. Each detector module 20 in a conventional system produces an analog electrical signal that represents the intensity of an incident X-ray beam and hence the attenuated beam as it passes through the patient 22. During a scan to acquire X-ray projection data, gantry 12 and the components mounted thereon rotate about a center of rotation 25 (e.g., isocenter) so as to collect attenuation data from a multitude of view angles relative to the imaged volume.

Rotation of gantry 12 and the operation of X-ray source 14 are governed by a control mechanism 26 of CT system 10. Control mechanism 26 includes an X-ray controller 28 that provides power and timing signals to an X-ray source 14, a collimator controller 29 that controls a width of an aperture of the pre-patient collimator 13 (and, thus, the size of the beam of X-rays 16), and a gantry motor controller 30 that controls the rotational speed and position of gantry 12. An image reconstructor 34 receives sampled and digitized X-ray data from DAS 32 and performs high-speed reconstruction. The reconstructed image is applied as an input to a computer 36, which stores the image in a mass storage device 38. Computer 36 also receives commands and scanning parameters from an operator via console 40. An associated display 42 allows the operator to observe the reconstructed image and other data from computer 36. The operator supplied commands and parameters are used by computer 36 to provide control signals and information to DAS 32, X-ray controller 28, collimator controller 29, and gantry motor controller 30. In addition, computer 36 operates a table motor controller 44, which controls a motorized table 46 to position patient 22 and gantry 12. Particularly, table 46 moves portions of patient 22 through a gantry opening or bore 48.

Figure 2:
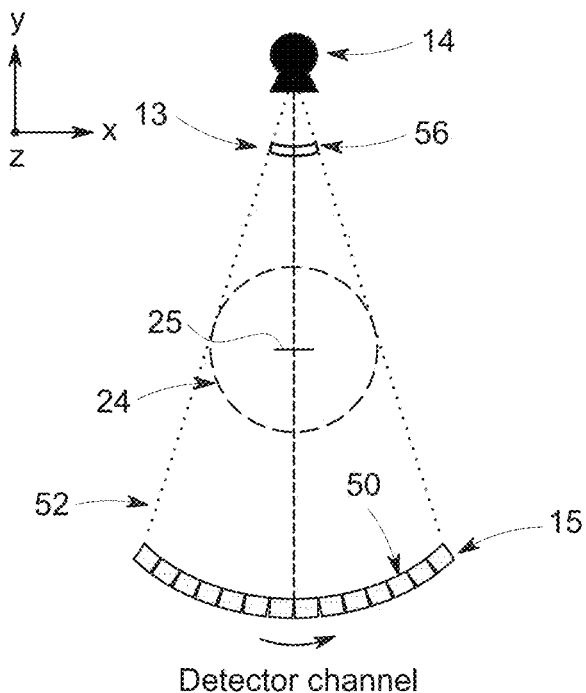
FIG. 2 is a schematic view of an X-ray source and a multi-row X-ray detector (e.g., as viewed in an X-Y plane), in accordance with aspects of the present disclosure.
Figure 3:
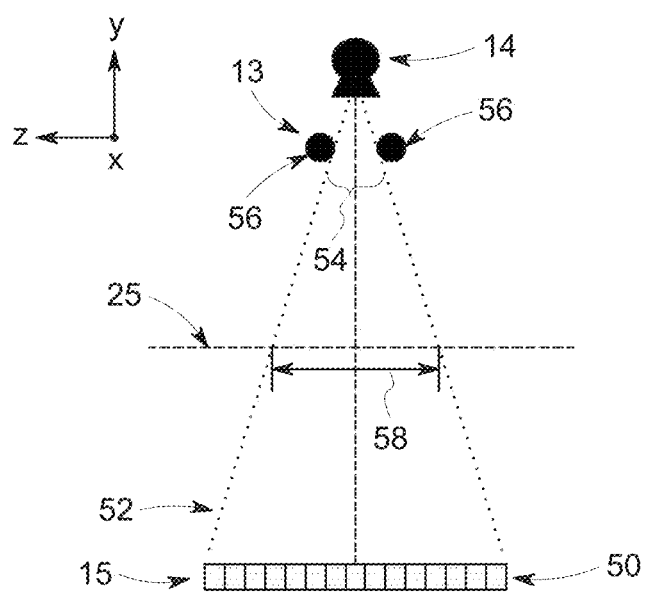
FIG. 3 is a schematic view of the X-ray source and the multi-row X-ray detector (e.g., as viewed in the Y-Z plane), in accordance with aspects of the present disclosure.

With the preceding discussion of an overall imaging system 10 in mind, and turning to FIGS. 2 and 3, an example of the X-ray source 14 and the detector assembly 15 (e.g., an X-ray detector having a plurality of rows 50) are illustrated in an X-Y plane (FIG. 2) and a Y-Z plane (FIG. 3), respectively. For convenience of explanation, the rotating gantry 12 with X-ray source 14 is rotated from the location shown in FIG. 1 to the top of the gantry (+Y direction). As depicted, the pre-patient collimator 13 is disposed between the X-ray source 14 and the detector assembly 15 and determines the shape of the X-ray beam 52. In particular, an opening or aperture 54 between a pair of collimator blades 56 of the pre-patient collimator 13 (as depicted in FIG. 3) shapes the X-ray beam 52. The field of view 24 and a beam width 58 corresponding to the size of the X-ray beam 52 intended for patient scanning are also illustrated. The correct positioning of the collimator blades 56 is important in ensuring that the patient receives the correct radiation dose and the correct area is scanned. The shape of the blades 56 are shown in different orientations in FIGS. 2 and 3. By way of example, the blades 56 are generally curved in the XY plane, with a circular leading edge in the YZ plane that determines the beam size. There are many other possible shapes of the blades in the XY plane including flat and angled; shapes of the leading edge in the YZ plane may also be rectangular or triangular, for example.

Figure 4:
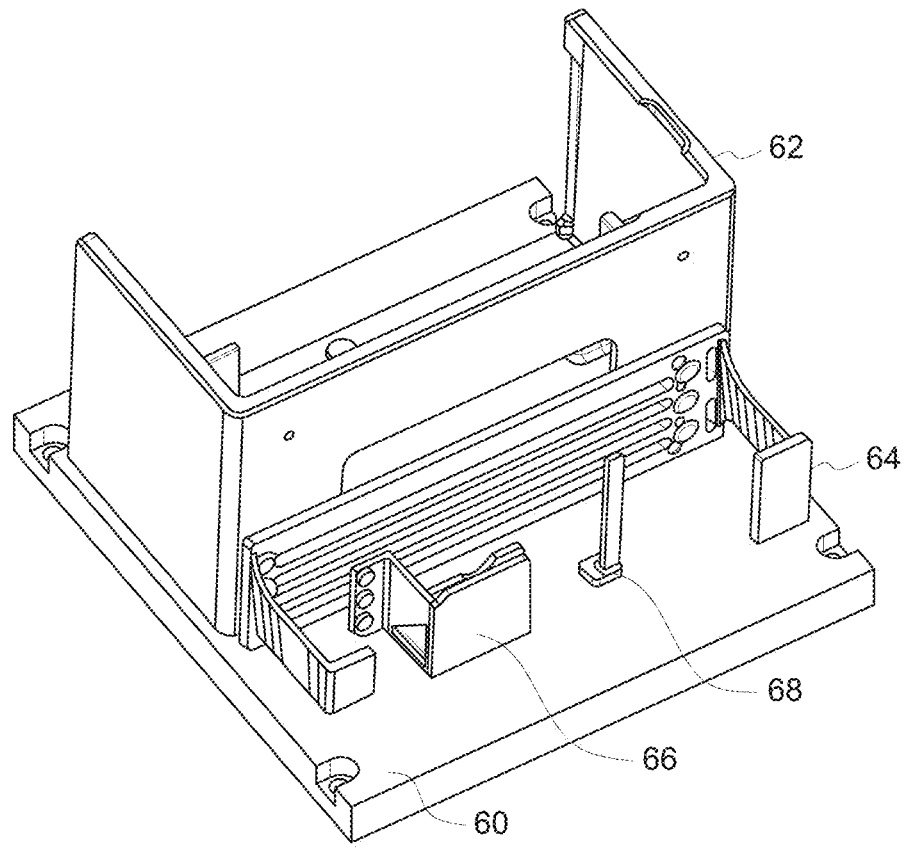
FIG. 4 is a perspective view of additively manufactured components of a collimator disposed on a print bed, in accordance with aspects of the present disclosure.
Figure 5:
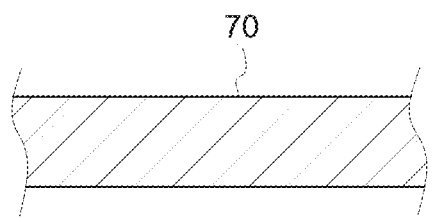
FIG. 5 is a cross-sectional view of a portion of a wall of an additively manufactured component of a collimator (e.g., of a solid structure), in accordance with aspects of the present disclosure.
Figure 6:
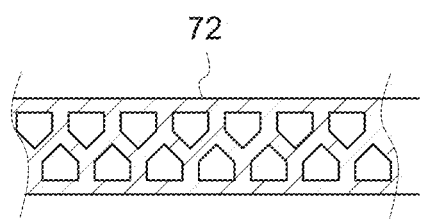
FIG. 6 is a cross-sectional view of a portion of a wall of an additively manufactured component of a collimator (e.g., of a lattice structure), in accordance with aspects of the present disclosure.
Figure 7:
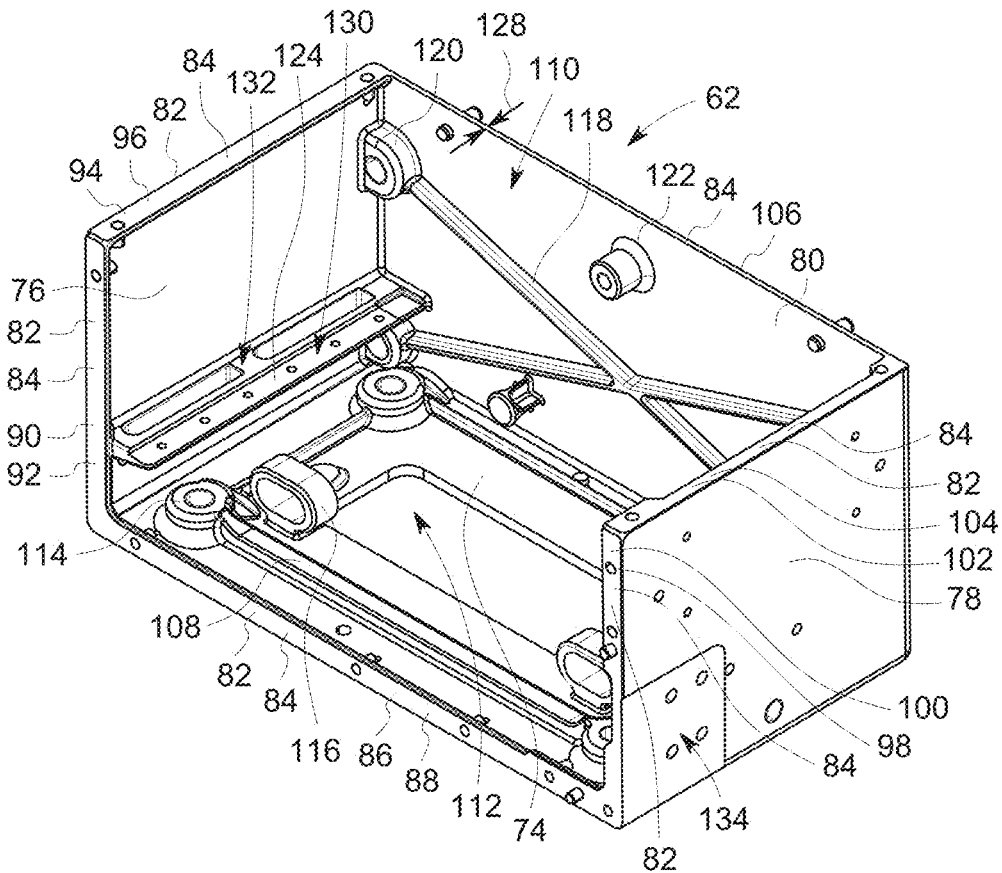
FIGS. 7-10 are different perspective views of an additively manufactured collimator housing, in accordance with aspects of the present disclosure.
Figure 8:
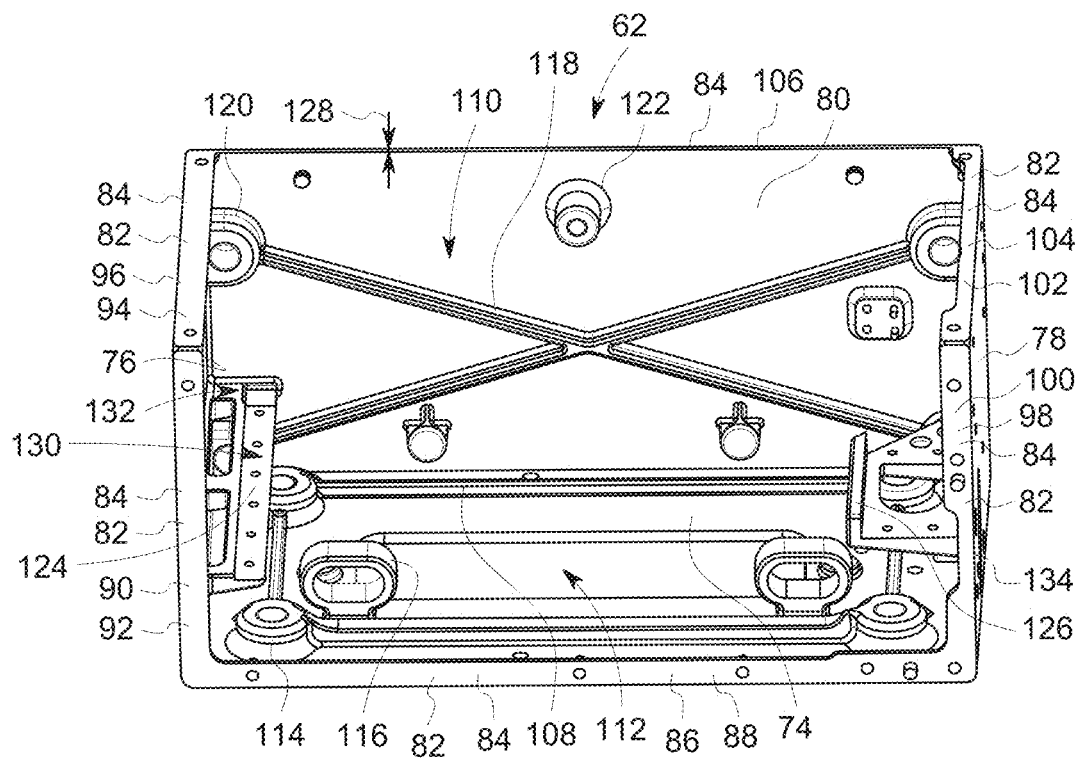
Figure 9:
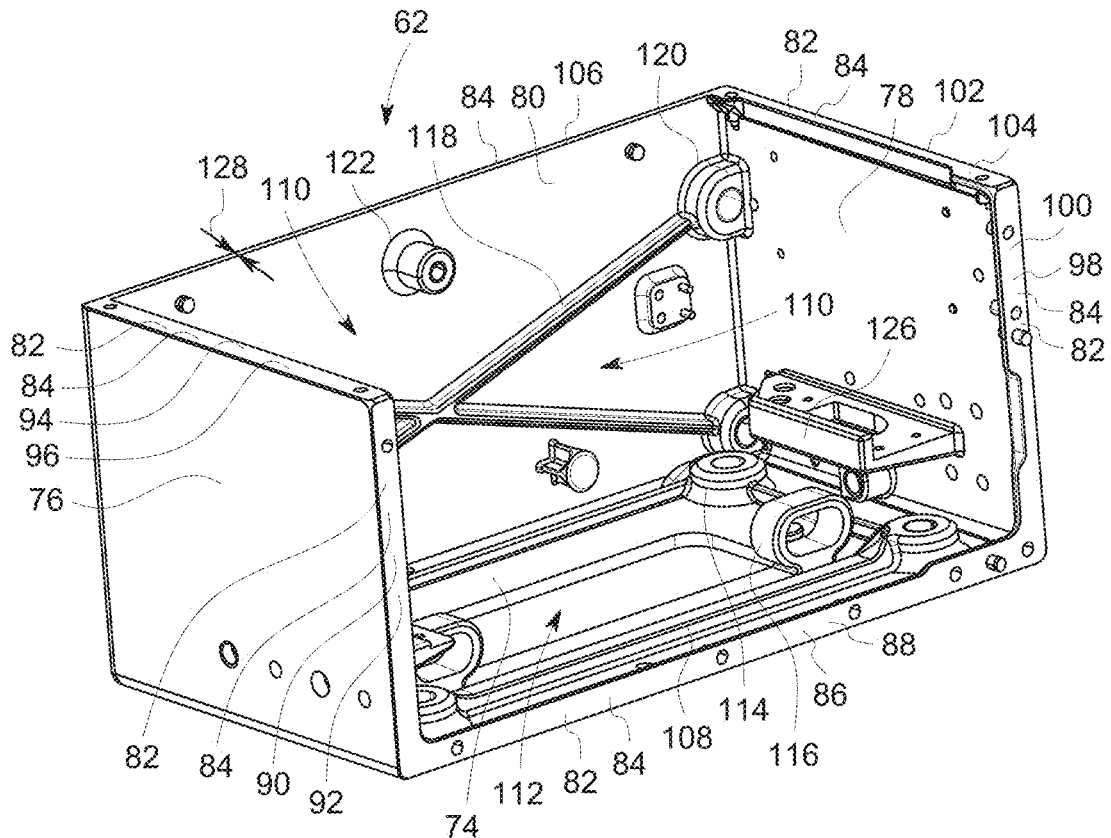

FIG. 4 is a perspective view of additively manufactured components of a pre-patient collimator disposed on a print bed 60. As depicted in FIG. 4, the additively manufactured components of the collimator include a collimator housing 62, an aperture carrier plate 64, a motor mounting plate 66, and a sensor plate 68. In certain embodiments, other components of the collimator may be additively manufactured (e.g., bowtie filter, plates or covers for housing the bowtie filter, cover plate for the collimator housing 62, etc.). The layout of the additively manufactured components on the print bed is one example of a layout configuration for the additive manufacturing or three-dimensional (3D) printing of the components of the collimator. Other layout configurations may be utilized. Each additively manufactured component is made of lead free material (e.g., to mitigate work hazards imposed by the presence of lead). In certain embodiments, the components may be formed of a metal material (e.g., via direct metal laser sintering). In certain embodiments, a portion or an entirety of an additively manufactured component may be made of a solid structure 70 as depicted in FIG. 5. For example, the entirely of the sensor plate 68 is made of a solid structure. The solid structure may function in X-ray blocking. In certain embodiments, a portion or entirety of an additively manufactured component may be made of a lattice structure 72 as depicted in FIG. 6. For example, the entirety of the motor mounting plate 66 is made of a lattice structure. The lattice structure enables weight reduction. The lattice structure may include a honeycomb structure or other lattice structure. As described in greater detail below, portions of the collimator housing 62 and the aperture carrier plate 64 are made of a lattice structure while other portions are made of a solid structure.

FIGS. 7-10 are different perspective views of the additively manufactured collimator housing 62. The collimator housing 62 includes a plurality of walls including a first wall 74 configured to face the X-ray source when the collimator is coupled to the gantry, a second wall 76 and a third wall 78 flanking the first wall 74, and a fourth wall 80 extending between the second wall 76 and the third wall 78 adjacent the first wall 74. Each wall 74, 76, 78, 80 includes a structural rib 82 (e.g., integral to the respective wall 74, 76, 78, 80) extending along at least one edge 84 of the walls 74, 76, 78, 80. For example, the first wall 74 includes a single structural rib 86 extending along an entirety of an edge 88. The second wall 76 includes a first structural rib 90 extending along an entirety of a first edge 92 (and extending from the rib 86) and a second structural rib 94 extending along an entirety of a second edge 96 (and extending from the rib 90). The third wall 86 includes a first structural rib 98 extending along an entirety of a first edge 100 (and extending from the rib 86) and a second structural rib 102 extending along an entirety of a second edge 104 (and extending from the rib 98). The fourth wall 80 includes the ribs 94 and 102 extending along portions of an edge 106 adjacent the second wall 76 and the third wall 78. The structural ribs 86 reduce deflection and eliminate stress concentrations at the corners of the collimator housing 62. In addition, the ribs 82 provide a mounting surface for covers to couple to the collimator housing 62.

Additional structural ribs 108 (e.g., integral to the first wall 74) are disposed on an inner surface of the first wall 74 and extend toward an interior space 110 of the collimator housing 62. The structural ribs 108 extend around a perimeter of an opening 112 for receiving an X-ray beam from the X-ray source when the collimator is coupled to the gantry and X-ray source. In particular, structural ribs 108 extend between structures 114 (e.g., integral to the first wall 74) that enable the collimator housing 62 to be coupled to the X-ray source via fasteners. The structures 114 also extend toward the interior space 110. The structural ribs 108 reduce both deflection and stress due to tube (X-ray source) centrifugal forces. The structural ribs 108 also contribute to the stiffness of the collimator housing 62. The design of the structural ribs 108 is self-supporting during additive manufacturing.

Figure 11:
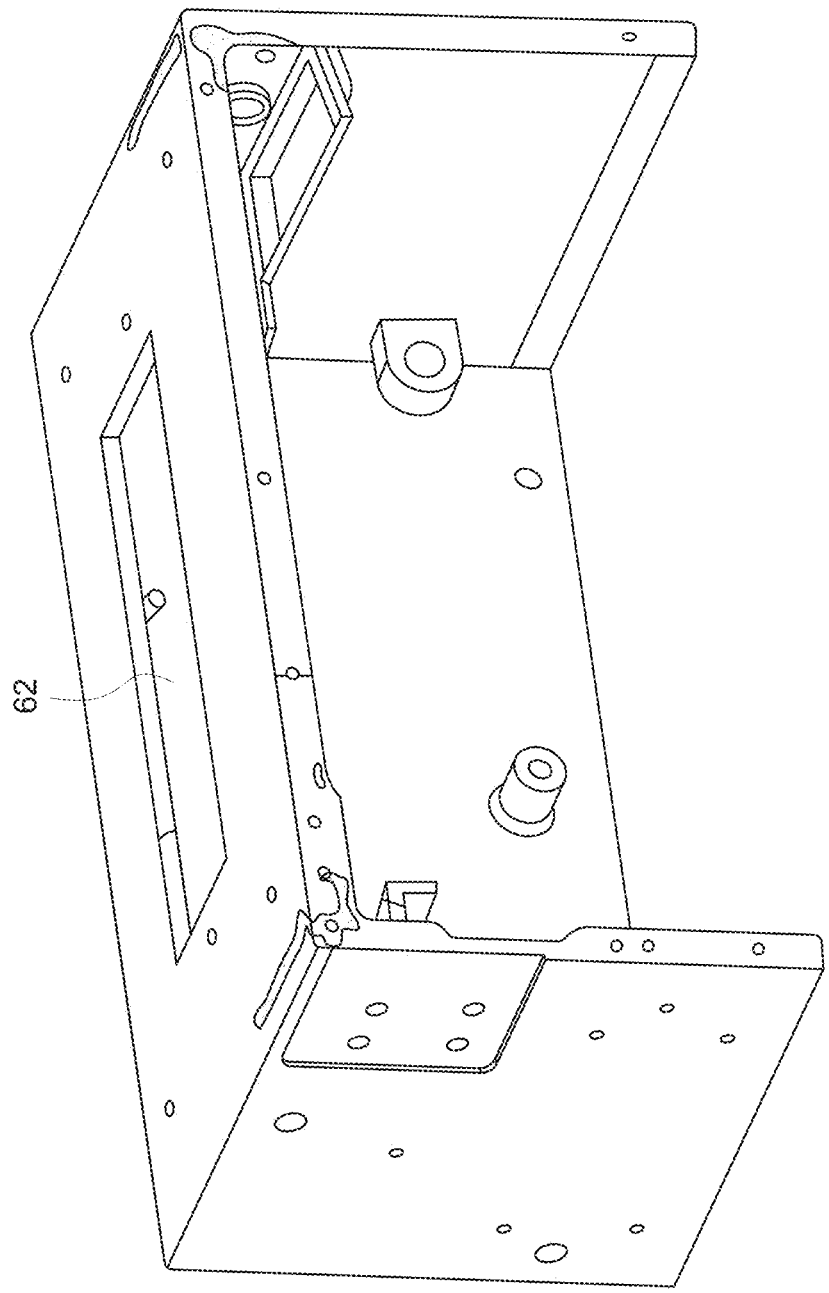
FIG. 11 is a stress plot of the collimator housing in FIGS. 7-10, in accordance with aspects of the present disclosure.
Figure 12:
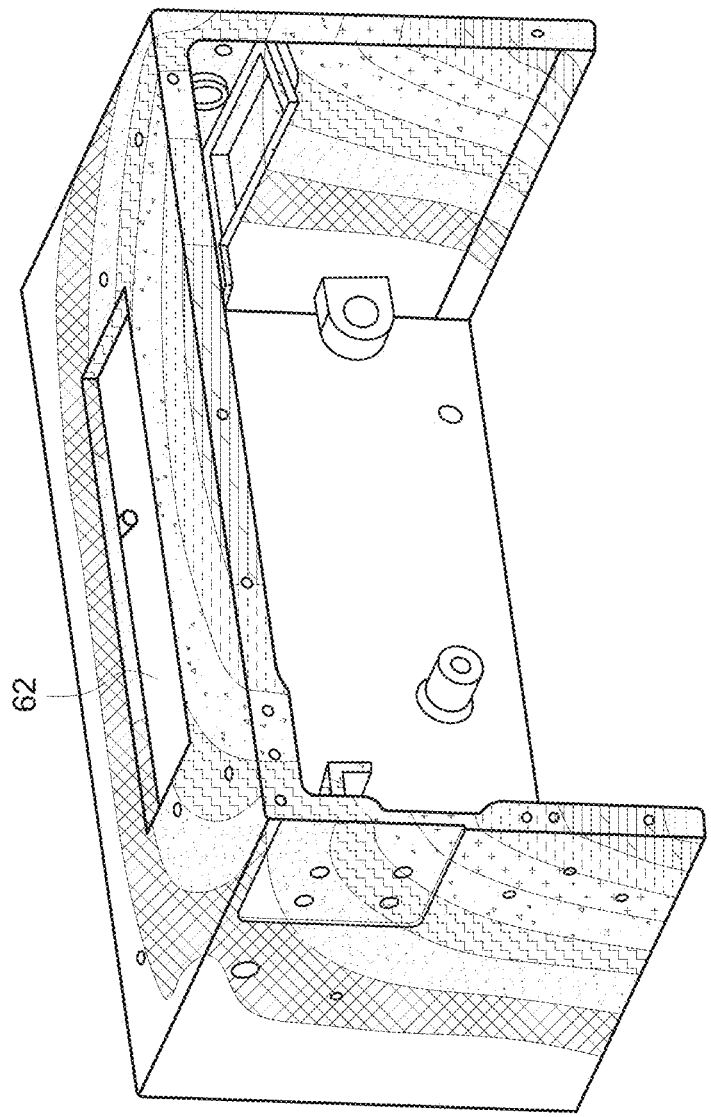
FIG. 12 is a deformation plot of the collimator housing in FIGS. 7-10, in accordance with aspects of the present disclosure.

The effect of the structural ribs 86, 108 on deflection and stress on the collimator housing 62 are depicted in FIGS. 11 and 12. FIGS. 11 and 12 are stress and deformation plots of the collimator housing 62, respectively, when the collimator housing 62 is coupled to a gantry and subjected to various load forces during rotation of the gantry. The ribs 86, 108 impart uniform stress distribution throughout the collimator housing 62 with only local stresses over small areas as depicted in FIG. 11. The ribs 86, 108 also impart a uniform and symmetric deflection on the collimator housing 62 as depicted in FIG. 12.

Returning to FIGS. 7-10, receptacles 116 (e.g., integral to the first wall 74) disposed on the interior surface of the first wall 74 flank the opening 112 and are configured so that guides for movement of a bowtie filter assembly can extend through them. The receptacles 116 also extend toward the interior space 110.

Further, stiffeners 118 (e.g., integral to the fourth wall 80) are disposed on an inner surface of the fourth wall 80. As depicted, the stiffeners 118 form an X-pattern. The pattern formed by the stiffeners 118 may vary. The stiffeners 118 add or provide stiffness to the collimator housing 62. In addition, the stiffeners 118 enable the collimator housing 62 to avoid warpage and shrinkage during manufacturing and post-processing operations. The stiffeners 118 extend between structures 120 (e.g., integral to the fourth wall 80) that enable the collimator housing 62 to be coupled to a gantry bearing. Some of the structures 120 are also partially disposed on an inner surface of either the second wall 76 or the third wall 78. The structures 120 also extend toward the interior space 110. An additional structure 122 (e.g., integral to the fourth wall 80) on the inner surface of the fourth wall 80 extends toward the interior space 110 is configured to receive a fastener to couple the bowtie filter assembly to the collimator housing 62.

Still further, a side structure 124 (e.g. integral to second wall 76) on the inner surface of the second wall 76 extends toward the interior space 110. The side structure 124 is configured to couple to a rail guide (e.g., directly to the rail guide) and an actuator (e.g., indirectly to the actuator via the rail guide) for the movement of the aperture carrier plate. A side structure 126 (e.g., integral to the third wall 78) disposed on the inner surface of the third wall 78 extends toward the interior space 110. The side structure 126 is also configured to couple to a rail guide (e.g., directly to the rail guide) and an actuator (e.g., indirectly to the actuator via the rail guide) for the movement of the aperture carrier plate.

Figure 10:
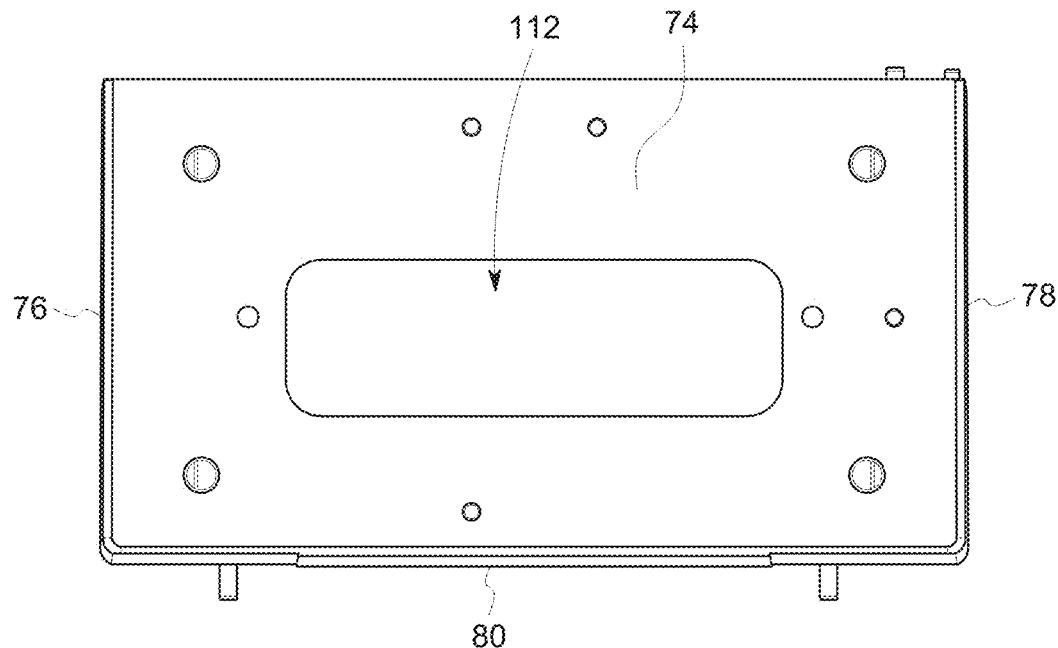

In certain embodiments, some of the structures extending from the inner surfaces of the walls 74, 76, 78, and 100 may be located in a different area or absent. In addition, due to the ribs 82 along the edges and the other structures extending toward the interior space 110 from the walls 74, 76, 78, and 80, a respective thickness 128 of each wall 74, 76, 78, and 80 may vary along its length. In addition, for certain walls, such as the fourth wall 80, in the areas where no structures or ribs are disposed, the thickness 128 of the fourth wall varies as illustrated in FIG. 10. Further, the respective thickness 128 of each wall 74, 76, 78, and 80 (in the areas where no structures or ribs are disposed) may be approximately 3.5 millimeters (which is approximately 5 to 35 percent of the thickness of a wall of a typical collimator housing).

In addition, some portions of the collimator housing 62 are made of a solid structure (as depicted in FIG. 5) and some portions of the collimator housing 62 are made of a lattice structure (as depicted in FIG. 6). With regard to the first wall 74, the structures 114 and the ribs 108 are made of a solid structure, while the rib 88, the receptacles 116 and the remainder of the first wall are made of a lattice structure. With regard the second wall 76, a first portion 130 (e.g., that couples directly to the rail guide) of the side structure 124 and the ribs 90, 94 are made of a lattice structure. A second portion 132 (e.g., closest to the inner surface of the second wall 76) of the side structure 124 and the remainder of the second wall 76 are made of a solid structure. With regard to the third wall 78, the ribs 98, 102, the side structure 126, and a corner portion 134 of the third wall 78 are made a lattice structure. The remainder of the third wall 78 is made of a solid structure. With regard to the fourth wall 80, the portions of the ribs 94, 102 along the edge 106 are made of a lattice structure. The remainder of the fourth wall 80 (including the stiffeners 118, the structures 120, and the structure 122) is made of a solid structure.

The utilization of solid structure in portions of the walls 74, 76, 78, and 80 provides for integrated, gapless X-ray shielding without additional attenuating material needing to be attached to the collimator housing 62. The gapless X-ray shielding keeps X-rays from exiting the pre-patient collimator except through an aperture of the of the aperture carrier plate 64. The utilization of the lattice structure enables the collimator housing 62 and the collimator to be lighter. For example, the collimator housing 62 may weigh approximately 3.3 kilograms (kg) which is approximately 23.5 percent the weight of a typical collimator housing. In addition, the footprint of the collimator housing 62 and the collimator is reduced. Due to the reduced footprint and weight of the collimator, the collimator may be handled with a single hand and easily torqued when coupling the collimator to the gantry.

Figure 13:
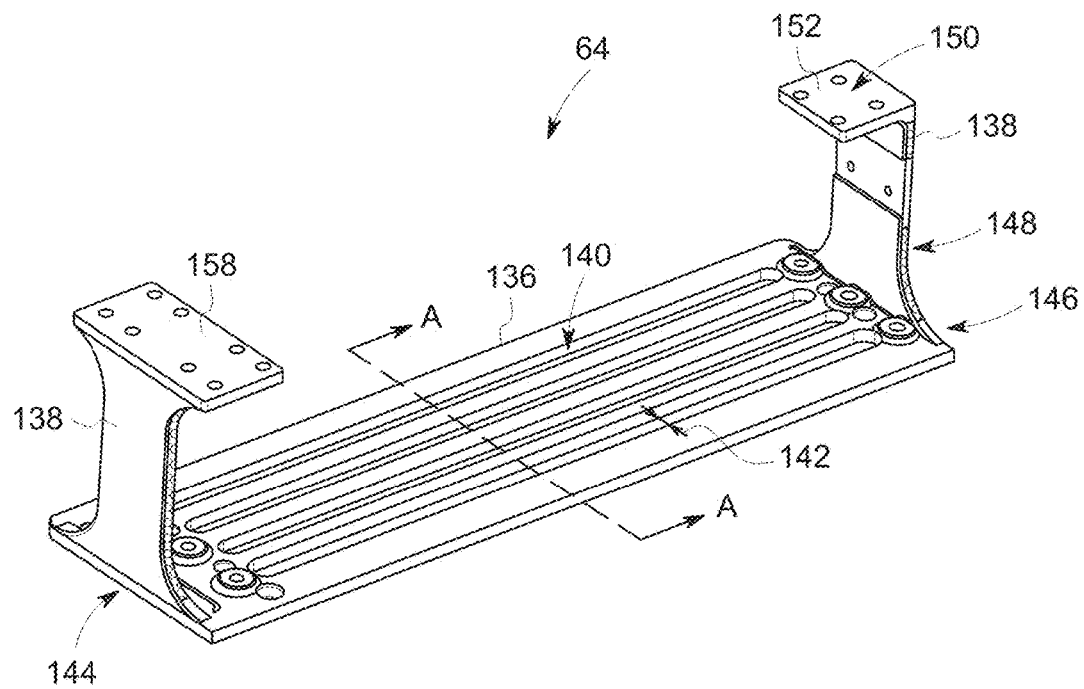
FIG. 13 is a perspective view of an additively manufactured aperture carrier plate, in accordance with aspects of the present disclosure.
Figure 14:
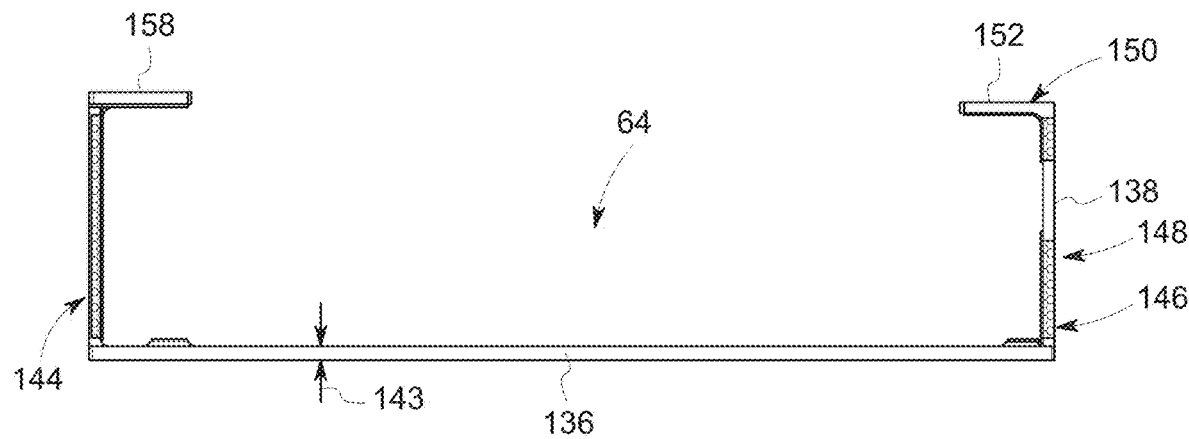
FIG. 14 is a side view of the additively manufactured aperture carrier plate in FIG. 13.
Figure 15:
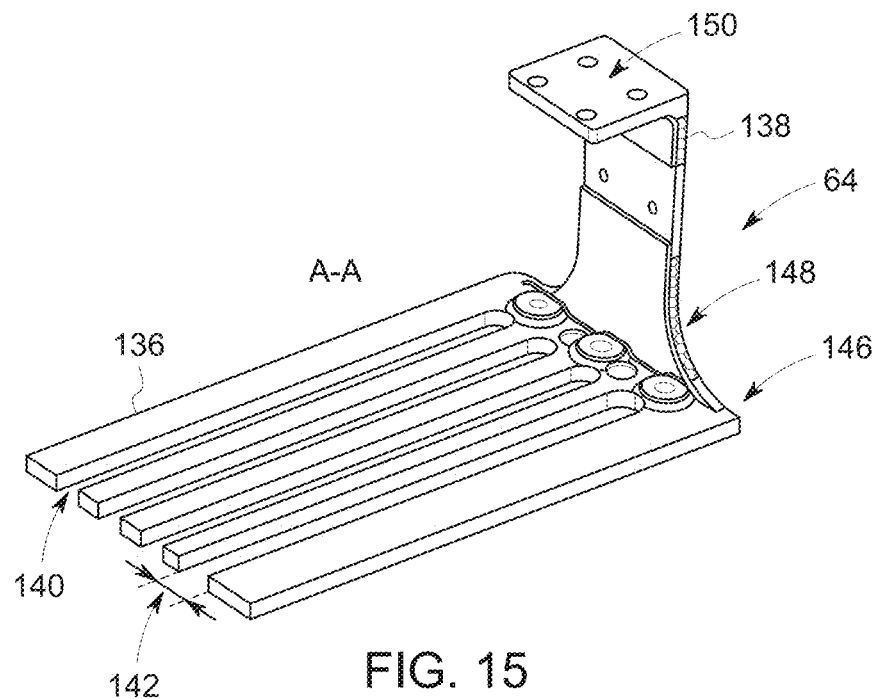
FIG. 15 is a cross-sectional view of a portion of the additively manufactured aperture carrier plate in FIG. 13, taken along line A-A.
Figure 16:
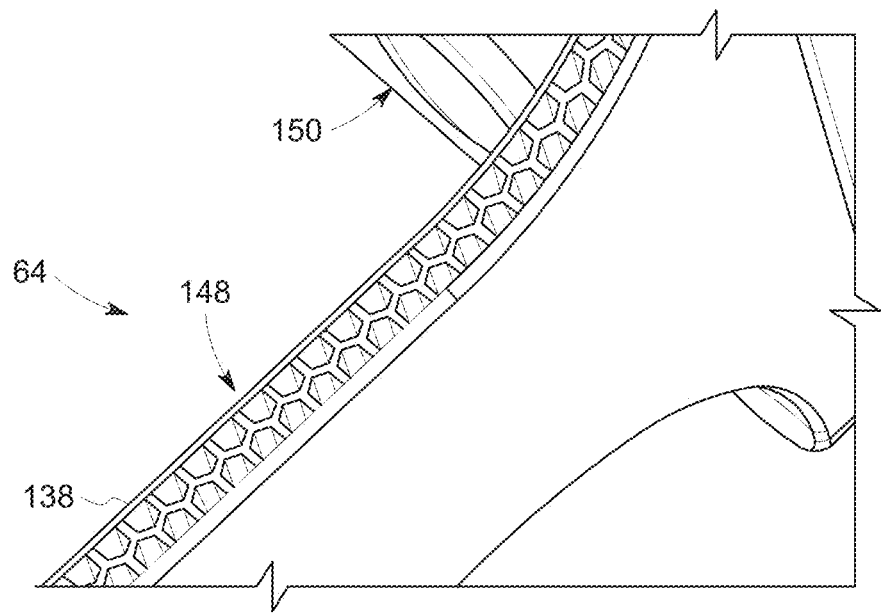
FIG. 16 is a perspective view of a portion of a mounting bracket of the additively manufactured aperture carrier plate in FIG. 13.

FIGS. 13 and 14 are views of the additively manufactured aperture carrier plate 64. The aperture carrier plate 64 includes a plate portion 136 and mounting brackets 138 integrated as a single piece. The plate portion 136 includes a plurality of apertures 140 with different widths 142. Which aperture 140 is utilized during emission—ray emission determines the size of the X-ray beam emitted from the collimator. The plate portion 136 varies in thickness 143 along its length. The plate portion 136 is made of solid structure (for X-ray attenuation) as depicted in FIG. 15. Returning to FIGS. 13 and 14, the mounting brackets 138 are located on longitudinal ends 144, 146 of the plate portion 136. Each mounting bracket 138 includes a first portion 148 extending perpendicular to the plate portion 136 and a second portion 150 extending parallel to the plate portion 136 and toward the other mounting bracket 138. Both portions 148, 150 are made of a lattice structure since these areas are not critical for X-ray attenuation. FIG. 16 illustrates the lattice structure in the second portion 150 of the mounting bracket 138.

Figure 17:
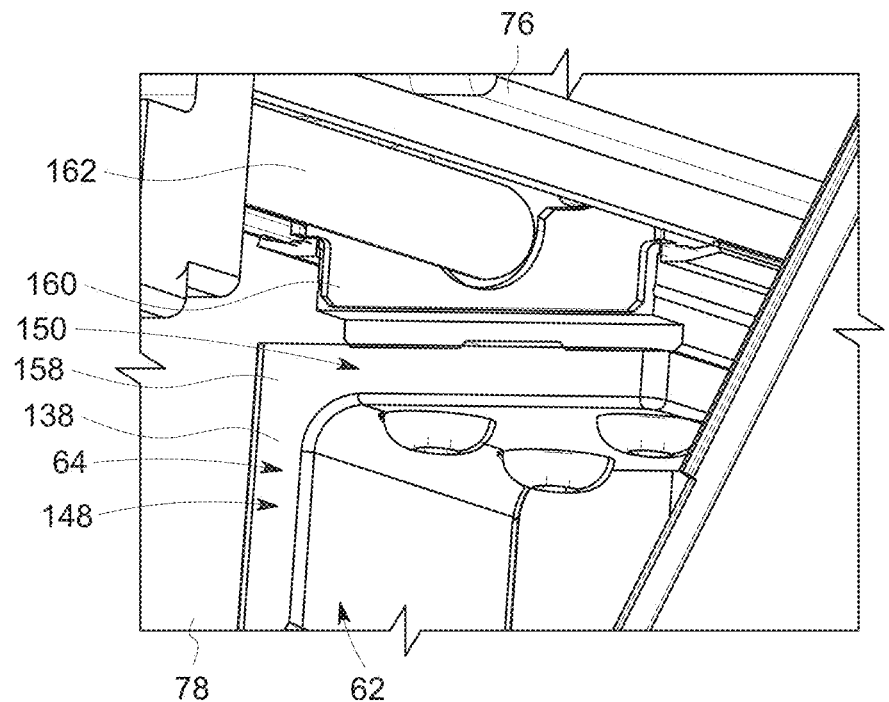
FIG. 17 is a perspective view of a mounting bracket of the additively manufactured carrier plate in FIG. 13 coupled to an actuator, in accordance with aspects of the present disclosure.
Figure 18:
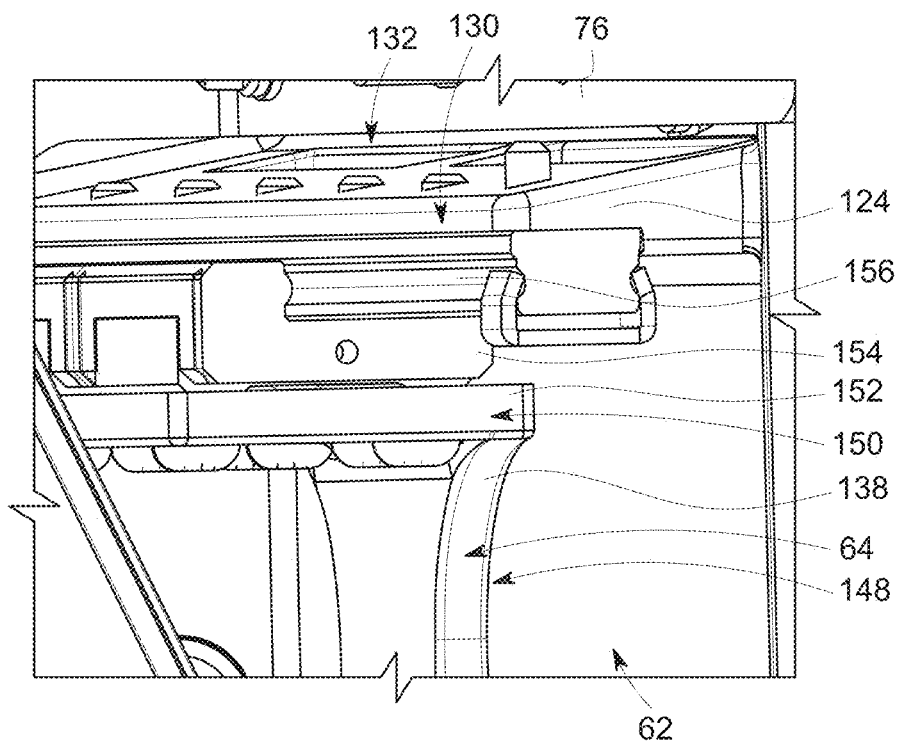
FIG. 18 is a perspective view of another mounting bracket of the additively manufactured carrier plate in FIG. 13 coupled to an actuator, in accordance with aspects of the present disclosure.

The second portions 150 of the mounting brackets 138 are configured to mount to actuators and rail guides that move the aperture carrier plate 64 into and out of the path of the X-ray beam (e.g., either mechanically or electrically). FIG. 17 illustrates the second portion 150 of a mounting bracket 152 (see FIGS. 13 and 14) coupled to an actuator 154 (e.g., via fasteners) which is coupled to a rail guide 156. The rail guide 156 is coupled to the side structure 124 within the collimator housing 62. The actuator 154 moves along the rail guide 56 to move the aperture carrier plate 64. FIG. 18 illustrates the second portion 50 of a mounting bracket 158 (see FIGS. 13 and 14) coupled to an actuator 160 (via fasteners) which is coupled to a rail guide 162. The rail guide 162 is coupled to the side structure 126 within the collimator housing 62. The actuator 160 may be driven by a motor which in turn drives movement of both actuators 154, 160 along their respective rails guides 156, 162 and, thus, movement of the aperture carrier plate 64.

Returning to FIGS. 13 and 14, the additively manufactured aperture carrier plate 64 may weigh approximately 0.3 kg which is approximately 23 percent of the weight of the multiple components that form a typical aperture carrier plate in a typical collimator. Additively manufacturing the additive carrier plate 64 eliminates spacer blocks and pins that are typically utilized in mounting of an aperture carrier plate within a typical collimator.

Utilizing additively manufactured components, significant mass reduction (e.g., 70 percent mass reduction compared to a typical collimator (e.g., lower cost collimator)), assembly time reduction (e.g., 50 percent compared to a typical collimator), cost reduction (e.g., 25 percent compared to a typical collimator), and increased part count efficiency (e.g., 81 percent reduction of total number of parts compared to a typical collimator) may be achieved. In addition, the reduced mass of the collimator utilizing additively manufactured components may reduce the CT rotating gantry mass, which translates into lesser power consumed by the gantry drive leading to significant reduction in operation cost (e.g., 17 to 18 percent compared to a typical collimator).

Figure 19:
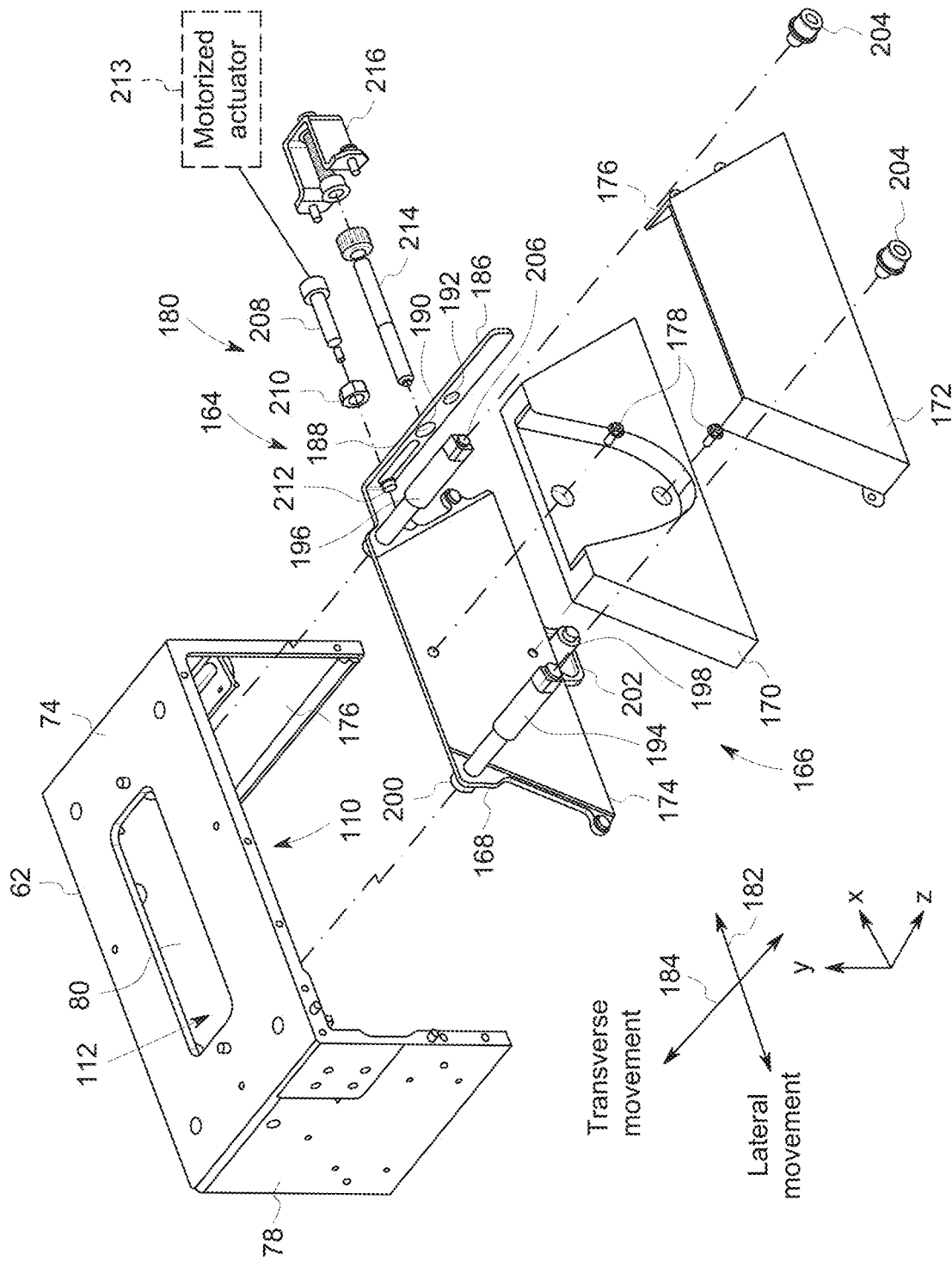
FIG. 19 is an exploded view of an in-built alignment mechanism for moving a bowtie filter assembly within a collimator housing, in accordance with aspects of the present disclosure.

Besides additively manufactured components, the prepatient collimator disclosed herein includes an in-built alignment mechanism to adjust positioning of a bowtie filter assembly. FIG. 19 is an exploded view of an in-built alignment mechanism 164 for moving a bowtie filter assembly 166 within the collimator housing 62. The bowtie filter assembly 166 includes a base plate or filter mounting plate 168, a bowtie filter 170 (e.g., made of polytetrafluoroethylene), and a cover 172 (e.g., front cover). The base plate 168 supports the bowtie filter 170 and components of the in-built alignment mechanism 164. The base plate 168 and the cover 172 partially enclose the bowtie filter 170 within. The cover 172 does not extend around a top and bottom portion of the bowtie filter 170. A radiation shielding layer 174 (e.g., made of a tungsten-based polymer) is disposed on the surface of the base plate 168 that directly interfaces with the bowtie filter 170. A radiation shielding layer 176 is disposed on the surfaces of the cover 172 that directly interface with the bowtie filter 170. The base plate 168 and the cover 172 are configured to house different types of bowtie filters 170. The bowtie filter 170 is coupled to or mounted to the base plate 168 via fasteners 178 (e.g., screws) that pass through corresponding openings on the bowtie filter 170 and the base plate 168. The cover 172 is coupled to or mounted to the base plate 168 to enclose the bowtie filter 170 via fasteners (not shown, e.g., screws) that pass through corresponding openings on cover 172 and the base plate 168.

The in-built alignment mechanism 164 includes an adjustment mechanism 180 configured to move the bowtie filter 170 in a first direction 182 (e.g., lateral direction or X-direction) and a second direction 184 (e.g., transverse direction or Z-direction, which is the same direction as CT table movement). The movement in the lateral direction 182 is independent of movement in the transverse direction 184. The movement in the lateral direction 182 occurs between the second wall 76 and the third wall 78 of the collimator housing 62. The movement in the transverse direction 184 occurs toward and away from the fourth wall 80 of the collimator housing 62. The lateral direction 182 is orthogonal to the transverse direction 184.

The adjustment mechanism 180 includes a frame 186 that is part of and extends from base plate 168. The single frame 186 enables motion in both the lateral direction 182 and the transverse direction 184 to be independent of each other. The frame 186 extends in the direction 184 parallel with the second wall 76 and the third wall 78. The frame 186 includes a slot 188 and a pair of openings 190, 192. The slot 188 is located closer to the fourth wall 80 of the collimator housing 62 than the openings 190, 192.

The in-built alignment mechanism 164 includes polymer guides 194, 196, and 198 for the bowtie filter assembly 166 to move along. Respective portions (e.g., threaded portions) of the polymers guides 194, 196 extend through openings on the base plate 168 and are coupled on a backside of the base plate 168 to the base plate 168 via fasteners 200 (e.g., nuts). The polymer guides 194, 196 extend through the receptacles 116 (see FIG. 8) on the first wall 74. The polymer guide 198 is coupled to a structure (e.g., structure 122 in FIG. 8) on the fourth wall 80. The polymer guide 198 extends through an opening 202 of the base plate 168. The receptacles 116 and the opening 202 define the range of movement of the bowtie filter assembly 166 in the lateral direction 182. Fasteners 204 (e.g., mounting screws) coupled to ends 206 (further away from the fourth wall 80) of the polymer guides 194, 196 limit the range of movement of the bowtie filter assembly 166 in the transverse direction 184. These fasteners 204 also hold the bowtie filter 170 firmly in the scan plane during operation. In certain embodiments, the fasteners 204 are loosened prior to adjustment in the lateral direction 182. In certain embodiments, the fasteners 204 are removed prior to adjustment in the transverse direction 184.

Figure 20:
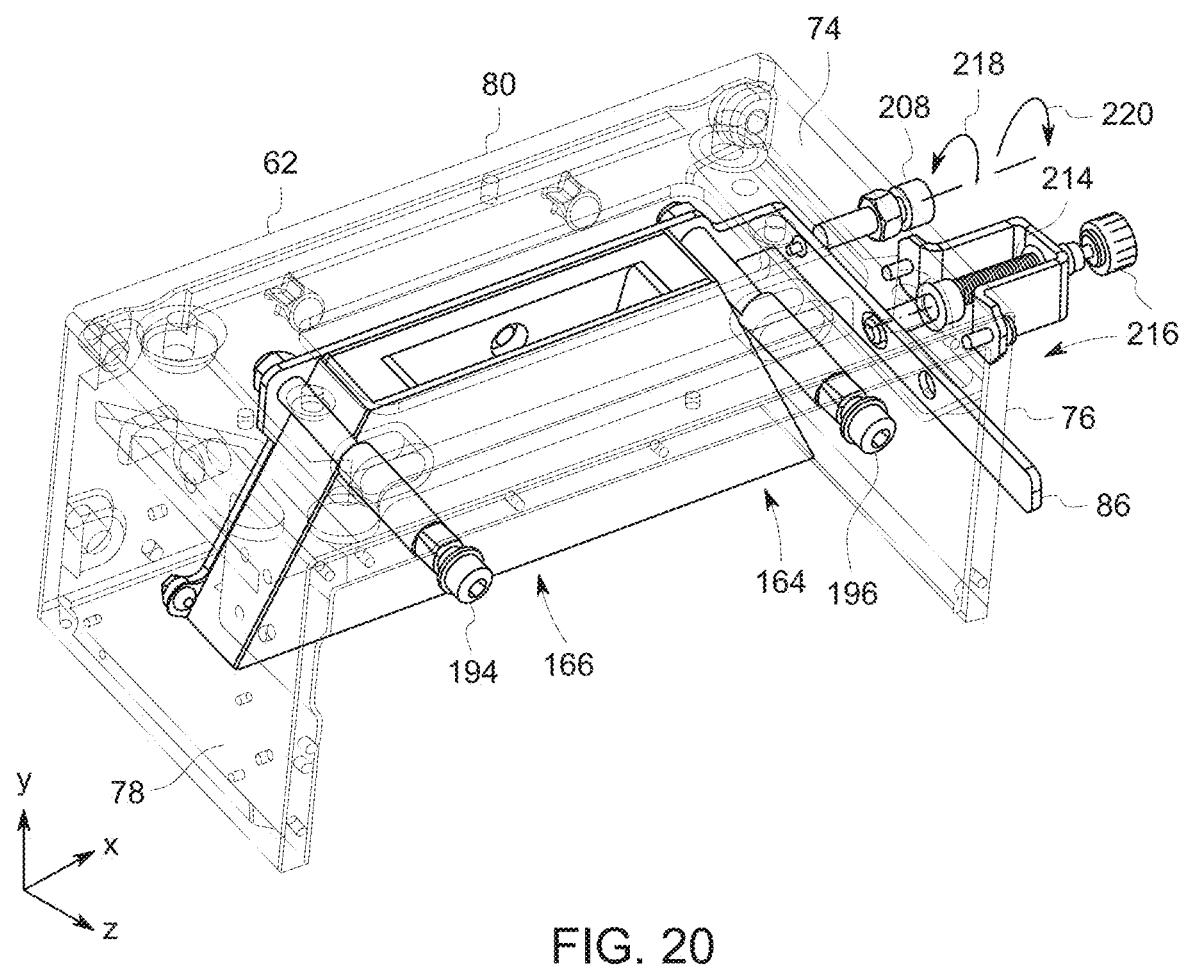
FIG. 20 is a perspective view of a collimator housing with a bowtie filter assembly within and coupled to an in-built alignment mechanism, in accordance with aspects of the present disclosure.
Figure 21:
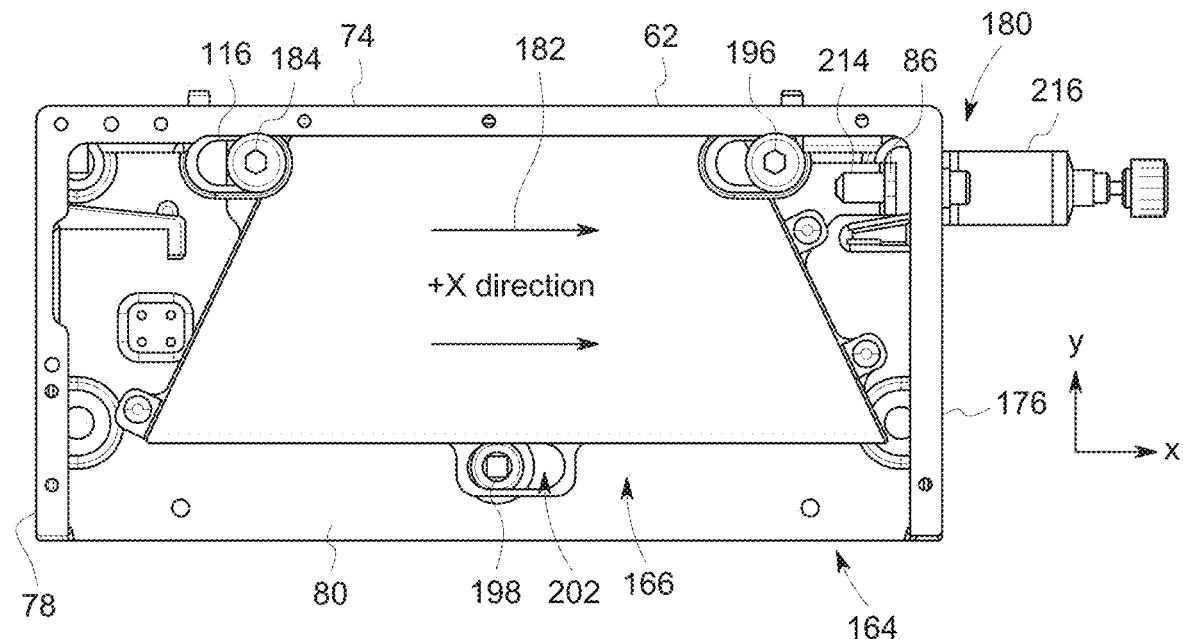
FIG. 21 is a front view of the collimator housing with the bowtie filter assembly within and coupled to the in-built alignment mechanism in FIG. 20 (e.g., with the bowtie filter assembly closer to a second wall of the collimator housing)
Figure 22:
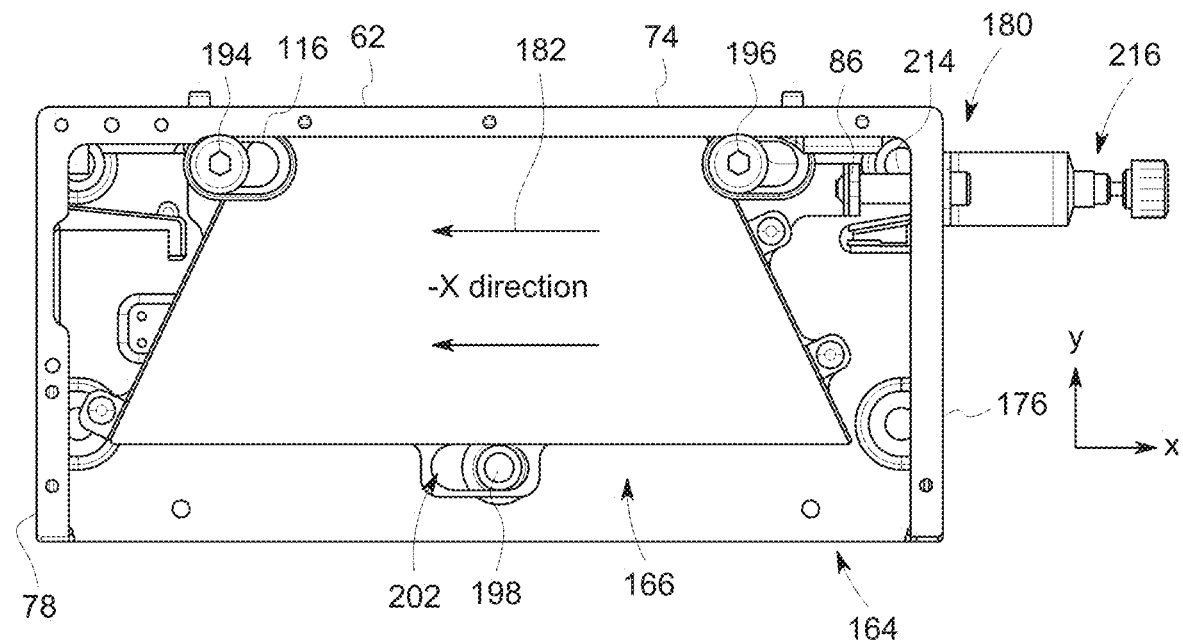
FIG. 22 is a front view of the collimator housing with the bowtie filter assembly within and coupled to the in-built alignment mechanism in FIG. 20 (e.g., with the bowtie filter assembly closer to a third wall of the collimator housing)

The adjustment mechanism 180 includes an adjustment screw 208 that adjusts movement of the bowtie filter assembly 166 in the lateral direction 182 within the collimator housing 62. The adjustment screw 208 enables adjusting the bowtie filter assembly 166 so that the bowtie filter 170 is in the isocenter of the X-ray beam. A portion of the adjustment screw 208 extends through a nut 210 (e.g., lock nut) on the outside of the collimator housing 62 and into the interior space 110 (via an opening in the second wall 76) of the collimator housing 62. Within the collimator housing 62, the portion of the adjustment screw 208 extends through the slot 188 and secured via a fastener 212 (e.g., nut) to the frame 186. Rotation of the adjustment screw 208 moves the bowtie filter assembly 166 in the lateral direction 182. Each end of the slot 188 acts as a limit on movement of the bowtie filter assembly 166 in the transverse direction 184. Once adjustment is complete, the lock nut 210 may be utilized to freeze the position of the bowtie filter assembly 166. The actuation of the adjustment screw 208 may be done mechanically. In certain embodiments, the actuation of the adjustment screw 208 may occur automatically via a motorized actuator 213 (in response to a control signal from processing circuitry of the collimator controller 29 in FIG. 1) coupled to the adjustment screw 208. As depicted in FIG. 20, rotation of the adjustment screw 208 in a circumferential direction 218 towards the fourth wall 80 results in movement of the bowtie filter assembly 166 in the lateral direction 182 (+X-direction) towards the second wall 76 as depicted in FIG. 21. As depicted in FIG. 20, rotation of the adjustment screw 208 in a circumferential direction 220 away from the fourth wall 80 results in movement of the bowtie filter assembly 166 in the lateral direction 182 (−X-direction) towards the third wall 78 as depicted in FIG. 22.

Figure 23:
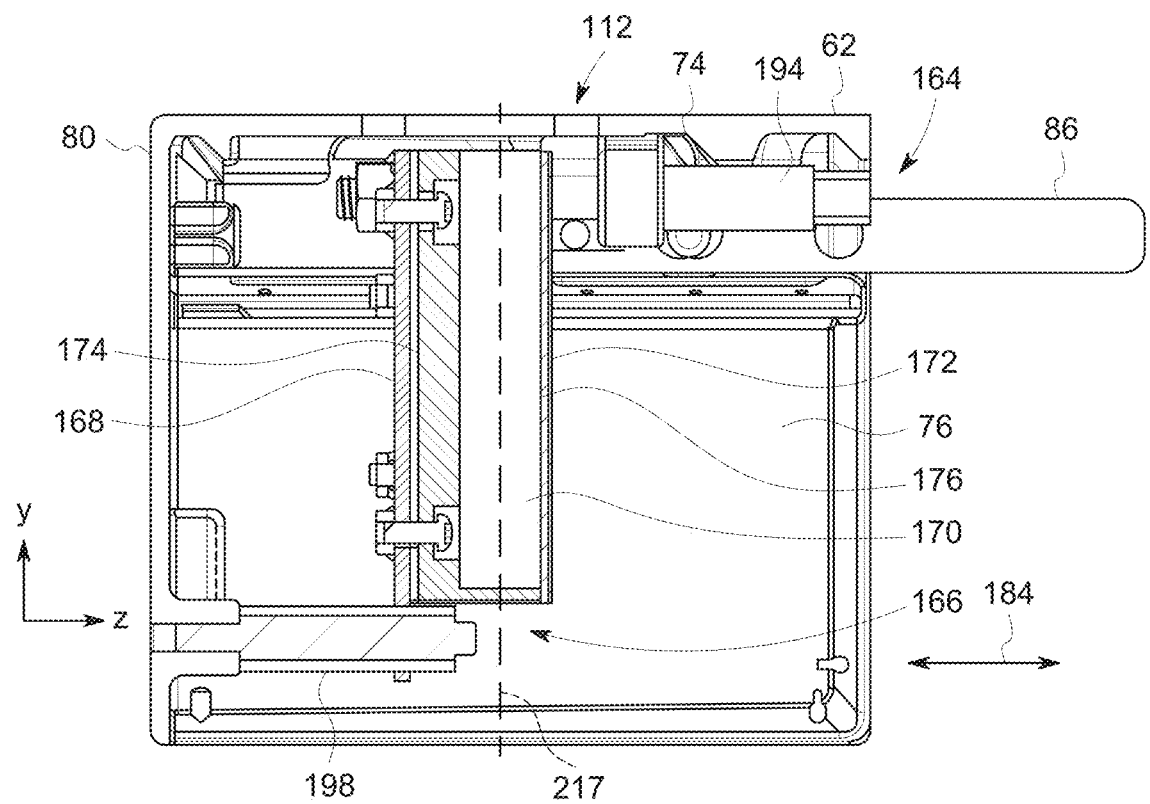
FIG. 23 is a cross-sectional side view of a collimator housing with a bowtie filter assembly within and coupled to an in-built alignment mechanism (e.g., having the bowtie filter assembly within a scan plane), in accordance with aspects of the present disclosure.
Figure 24:
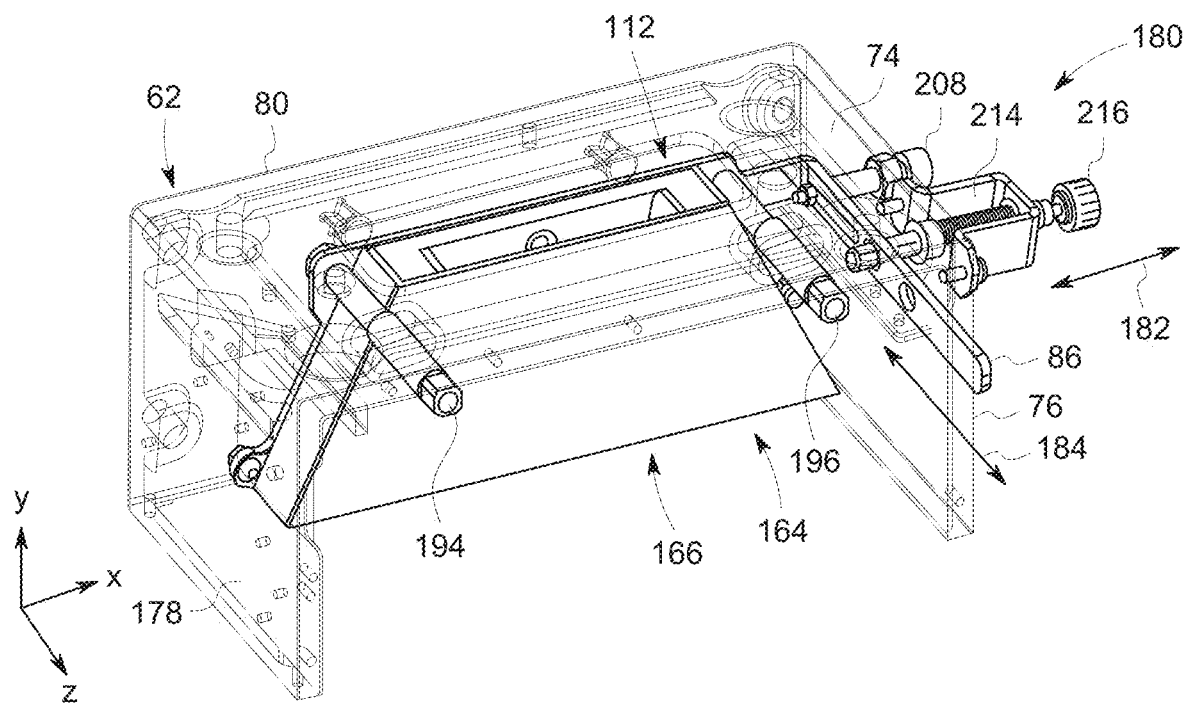
FIG. 24 is perspective view of the collimator housing with the bowtie filter assembly within and coupled to the in-built alignment mechanism in FIG. 23 (e.g., having the bowtie filter assembly within the scan plane)
Figure 25:
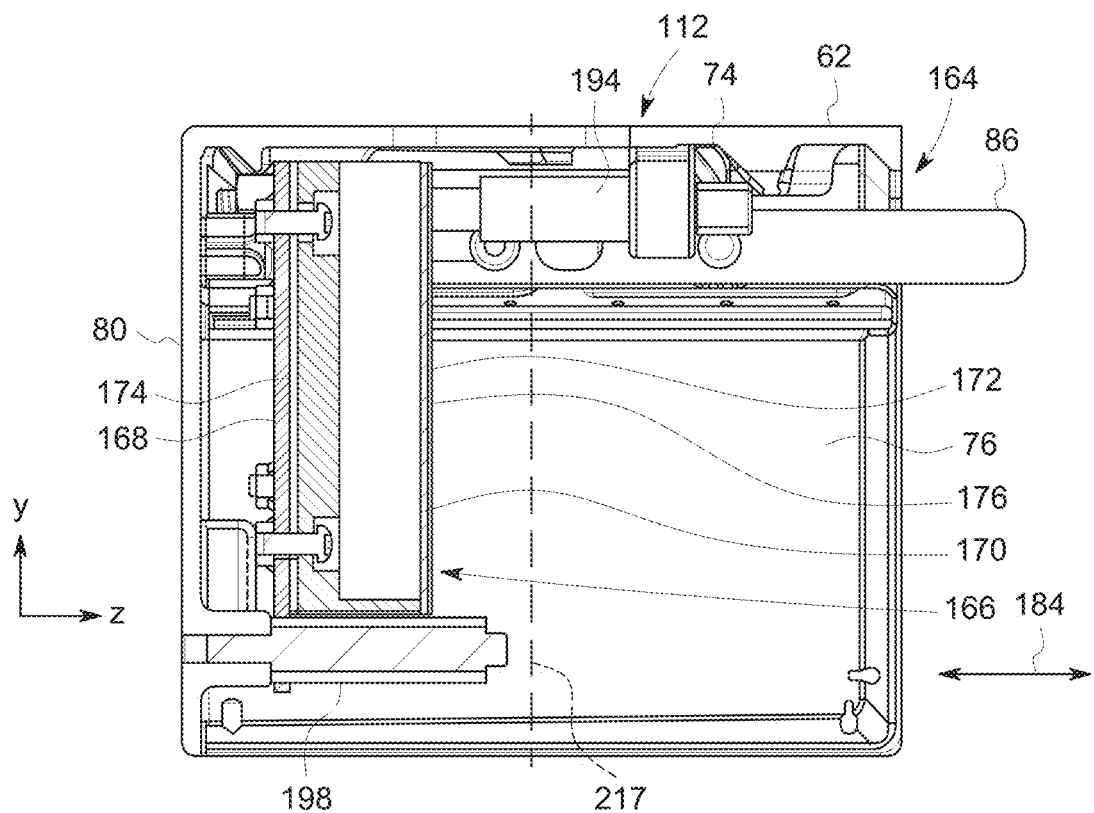
FIG. 25 is cross-sectional side view of the collimator housing with the bowtie filter assembly within and coupled to the in-built alignment mechanism in FIG. 23 (e.g., having the bowtie filter assembly outside of the scan plane)
Figure 26:
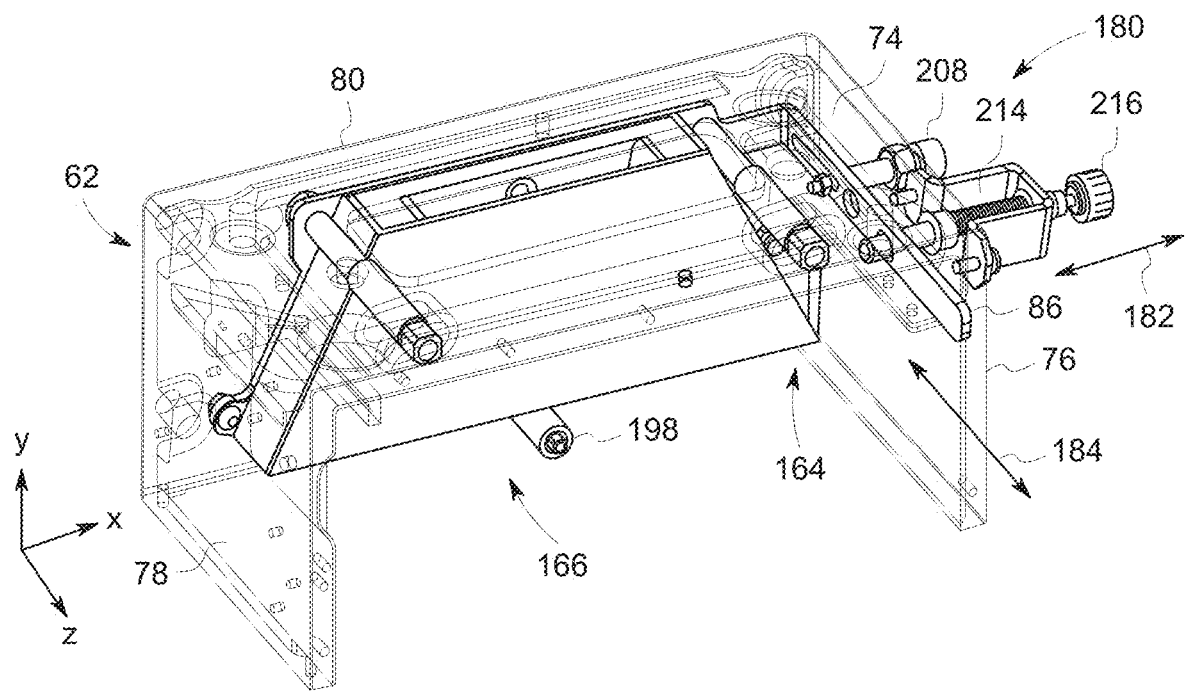
FIG. 26 is perspective view of the collimator housing with the bowtie filter assembly within and coupled to the in-built alignment mechanism in FIG. 23 (e.g., having the bowtie filter assembly outside of the scan plane)

Returning to FIG. 19, the adjustment mechanism 180 also includes a lock pin 214 coupled to a lock pin spring mechanism 216 that adjusts movement of the bowtie filter assembly 166 in the transverse direction 184 within the collimator housing 62. The lock pin spring mechanism 216 is located outside of the collimator housing 62. The lock pin 214 extends from outside the collimator housing 62 into the interior space 110 (via an opening in the second wall 76) of the collimator housing 62. A portion of the lock pin 214 extends through one of the openings 190, 192 of the frame 186. When the lock pin 214 is disposed in the opening 190, the bowtie filter assembly 166 is positioned so that the bowtie filter 170 is aligned within a scan plane 217 (through opening 112 in the first wall 74) as depicted in FIGS. 23 and 24. When the lock pin 214 is disposed in the opening 192, the bowtie filter assembly 166 is located closer to the fourth wall 80 and outside the scan plane 217 as depicted in FIGS. 25 and 26. Movement of the lock pin mechanism 216 away from the collimator housing 62 withdraws the lock pin 214 from whichever opening the 190, 192 the lock pin 214 was disposed in and enables the bowtie filter assembly 166 to be moved in the transverse direction 184 along the polymer guides 194, 196, and 198. Releasing the lock pin mechanism 216 enables the lock pin 214 to extend through a desired opening 190, 192 when aligned with it. The actuation of the lock pin mechanism 216 may be done mechanically or automatically via a motorized actuator.

Figure 27:
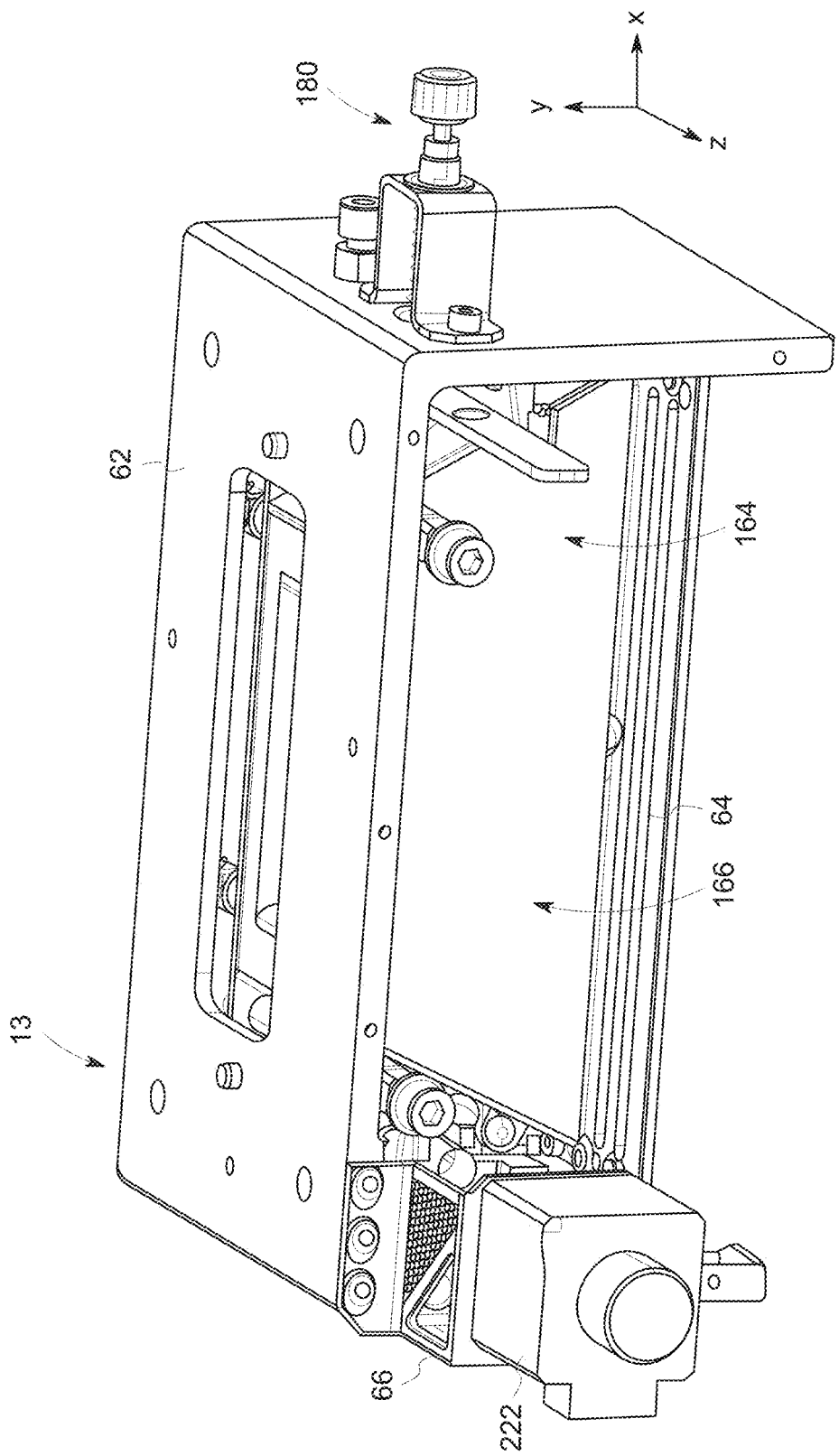
FIG. 27 is a perspective view of an assembled pre-patient collimator, in accordance with aspects of the present disclosure.

FIG. 27 is a perspective view of an assembled pre-patient collimator 13. The collimator 13 includes the additively manufactured collimator housing 62, the additively manufactured aperture carrier plate 64, and the additively manufactured motor mounting plate 66 described above. In addition, the collimator 13 includes the in-built alignment mechanism 164, the adjustment mechanism 180, and a motor 222 coupled to the motor mounting plate 66 and configured to move the aperture carrier plate 64 (via actuators and rail guides).

Figure 28:
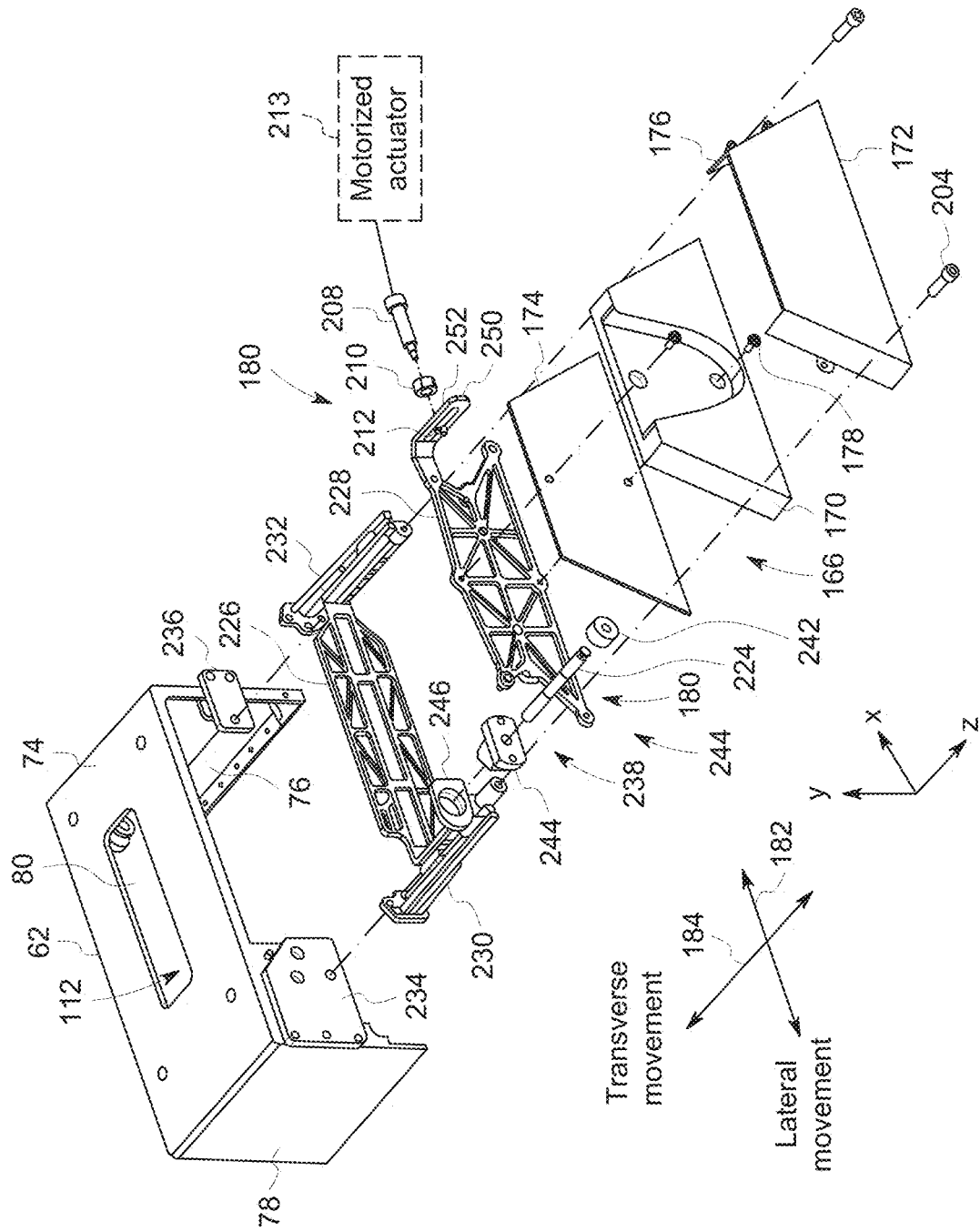
FIG. 28 is an exploded view of another in-built alignment mechanism for moving a bowtie filter assembly within a collimator housing, in accordance with aspects of the present disclosure.

FIG. 28 is an exploded view of another in-built alignment mechanism 224 for moving a bowtie filter assembly 166 within the collimator housing 62. The in-built alignment mechanism 224 includes a base plate 226 coupled to the bowtie filter assembly 166. The bowtie filter assembly 166 includes a filter mounting plate 228, a bowtie filter 170 (e.g., made of polytetrafluoroethylene), and a cover 172 (e.g., front cover). The base plate 168 supports the bowtie filter assembly 166 and components of the in-built alignment mechanism 224. The filter mounting plate 228 and the cover 172 partially enclose the bowtie filter 170 within. The cover 172 does not extend around a top and bottom portion of the bowtie filter 170. A radiation shielding layer 174 (e.g., made of a tungsten-based polymer) is disposed on the surface of the filter mounting plate 228 that directly interfaces with the bowtie filter 170. A radiation shielding layer 176 is disposed on the surfaces of the cover 172 that directly interface with the bowtie filter 170. The filter mounting plate 228 and the cover 172 are configured to house different types of bowtie filters 170. The bowtie filter 170 is coupled to or mounted to the filter mounting plate 228 via fasteners 178 (e.g., screws) that pass through corresponding openings on the bowtie filter 170 and the filter mounting plate 228. The cover 172 is coupled to or mounted to the filter mounting plate 228 to enclose the bowtie filter 170 via fasteners (not shown, e.g., screws) that pass through corresponding openings on the cover 172 and the filter mounting plate 228.

The in-built alignment mechanism 224 includes an adjustment mechanism 180 configured to move the bowtie filter assembly 166 in a first direction 182 (e.g., lateral direction) and a second direction 184 (e.g., transverse direction). The movement in the lateral direction 182 is independent of movement in the transverse direction 184. The movement in the lateral direction 182 occurs between the second wall 76 and the third wall 78 of the collimator housing 62. The movement in the transverse direction 184 occurs toward and away from the fourth wall 80 of the collimator housing 62. The lateral direction 182 is orthogonal to the transverse direction 184.

Figure 29:
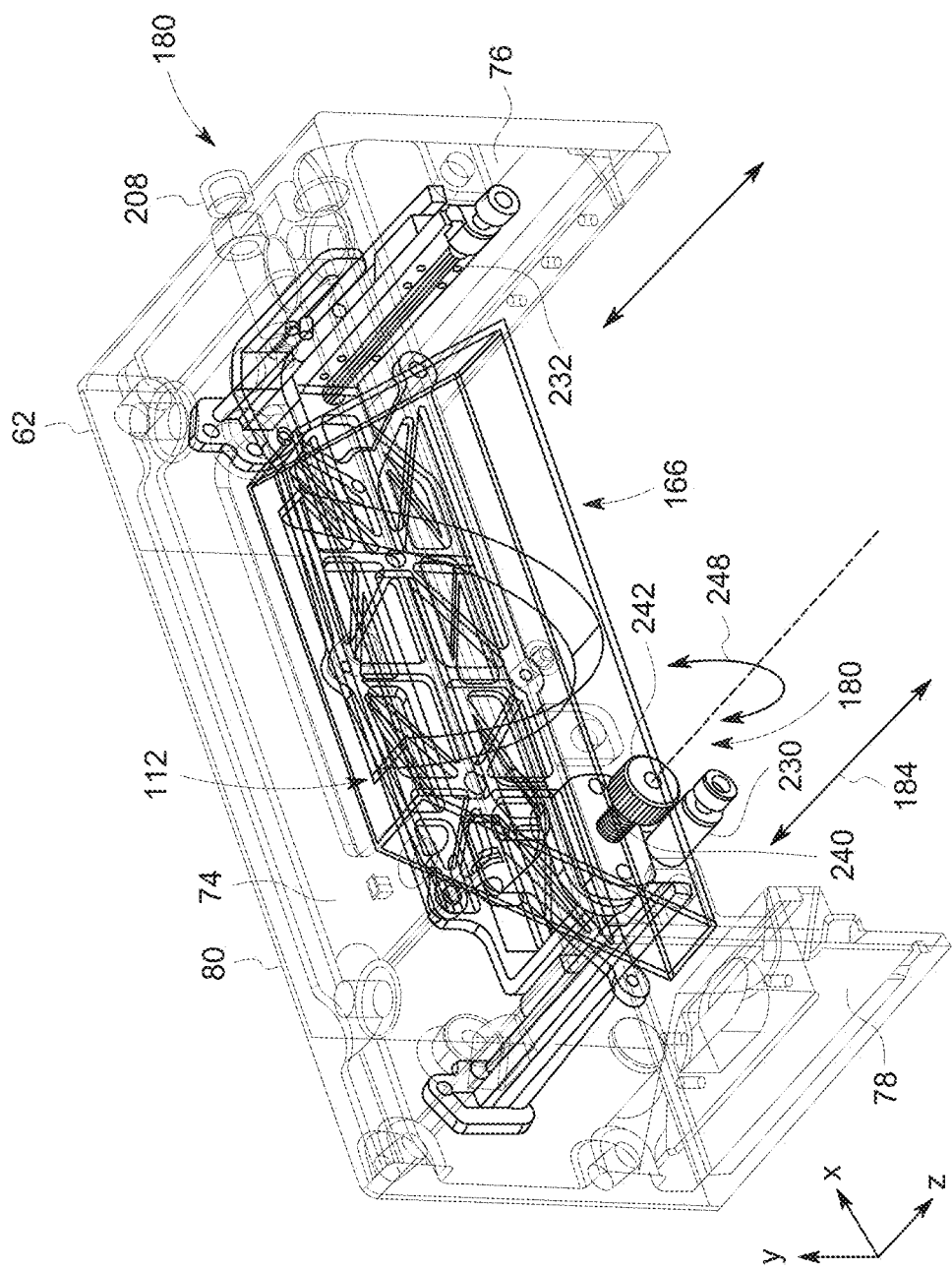
FIG. 29 is a front perspective view of a collimator housing with a bowtie filter assembly within and coupled to an in-built alignment mechanism (e.g., illustrating transverse movement of the bowtie filter assembly), in accordance with aspects of the present disclosure.

The in-built alignment mechanism 224 includes surface contact rail guides 230, 232 for the bowtie filter assembly 166 and the base plate 226 to move along. The surface contact rail guides 230, 232 are respectively coupled to mounting plates 234, 236 which are mounted to the fourth wall 80 of the collimator housing 62. The base plate 226 is disposed on the surface contact rail guides 230, 232. The adjustment mechanism 180 includes an actuator screw assembly 238 that includes an actuator screw 240, a knob 242 coupled to the actuator screw 240, and a receptacle 244 that includes a threaded portion. The receptacle 244 is mounted to receptacle portion 246 of the base plate 226 that includes an opening for the threaded portion of the receptacle 244. The actuator screw 240 is configured to move in and out of the threaded portion of the receptacle to move the bowtie filter assembly 166 in the transverse direction 184 along the surface contact rail guides 230, 232 (e.g., into and out of the scan plane). The actuation of the actuator screw 240 may be done mechanically or automatically via a motorized actuator. Actuation of the actuator screw 240 (via the knob 242) as indicated by arrow 248 in FIG. 29, results in movement in the transverse direction 184 of the bowtie filter assembly 166 and the base plate 226. Fasteners 204 (e.g., mounting screws) coupled to ends 206 (further away from the fourth wall 80) of the surface contact rail guides 230, 232 limit the range of movement of the bowtie filter assembly 166 in the transverse direction 184. These fasteners 204 also hold the bowtie filter 170 firmly in the scan plane during operation.

The adjustment mechanism 180 includes a frame 250 that is part of and extends from the filter mounting plate 228. The frame 250 enables motion of the bowtie filter assembly 166 in the lateral direction 182 which is independent of the movement in the transverse direction 184. The frame 250 extends in the direction 184 parallel with the second wall 76 and the third wall 78. The frame 250 includes a slot 252.

Figure 30:
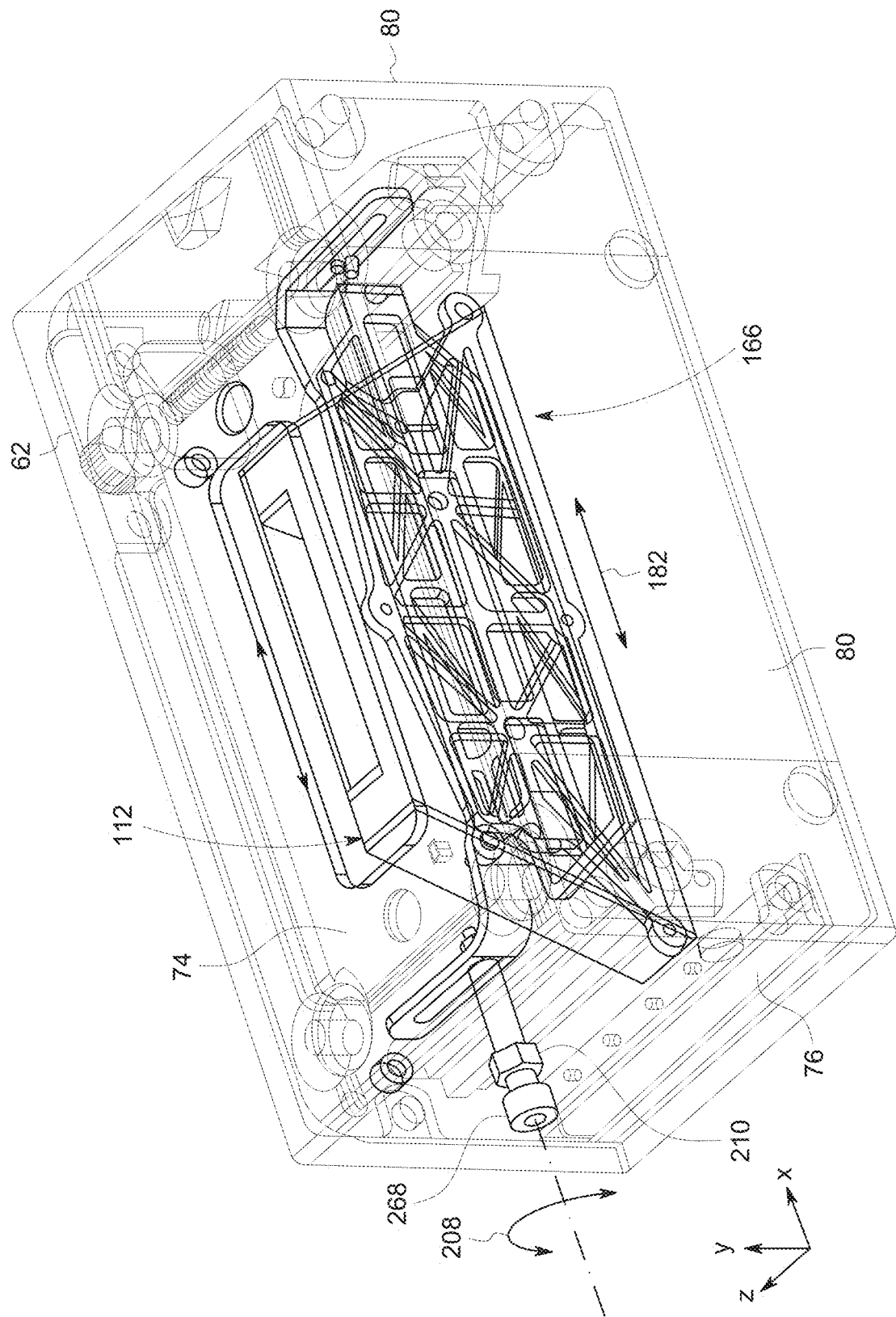
FIG. 30 is a rear perspective view of a collimator housing with a bowtie filter assembly within and coupled to an in-built alignment mechanism (e.g., illustrating lateral movement of the bowtie filter assembly), in accordance with aspects of the present disclosure.

The adjustment mechanism 180 includes an adjustment screw 208 that adjusts movement of the bowtie filter assembly 166 in the lateral direction 182 within the collimator housing 62 (without movement of the base plate 226). The adjustment screw 208 enables adjusting the bowtie filter assembly 166 so that the bowtie filter 170 is in the isocenter of the X-ray beam. A portion of the adjustment screw 208 extends through a nut 210 (e.g., lock nut) on the outside of the collimator housing 62 and into the interior space 110 (via an opening in the second wall 76) of the collimator housing 62. Within the collimator housing 62, the portion of the adjustment screw 208 extends through the slot 252 and secured via a fastener 212 (e.g., nut) to the frame 250. Rotation of the adjustment screw 208 moves the bowtie filter assembly 166 in the lateral direction 182. Each end of the slot 252 acts as a limit on movement of the bowtie filter assembly 166 in the transverse direction 184. Once adjustment is complete, the lock nut 210 may be utilized to freeze the position of the bowtie filter assembly 166. The actuation of the adjustment screw 208 may be done mechanically. In certain embodiments, the actuation of the adjustment screw 208 may occur automatically via a motorized actuator 213 (in response to a control signal from processing circuitry of the collimator controller 29 in FIG. 1) coupled to the adjustment screw 208. As depicted in FIG. 30, rotation of the adjustment screw 208 in a circumferential direction (indicated by arrow 254) towards the fourth wall 80 results in movement of the bowtie filter assembly 166 in the lateral direction 182 towards the second wall 76 while rotation of the adjustment screw 208 in the circumferential direction away from the fourth wall 80 results in movement of the bowtie filter assembly 166 in the lateral direction 182 towards the third wall 78.

Figure 31:
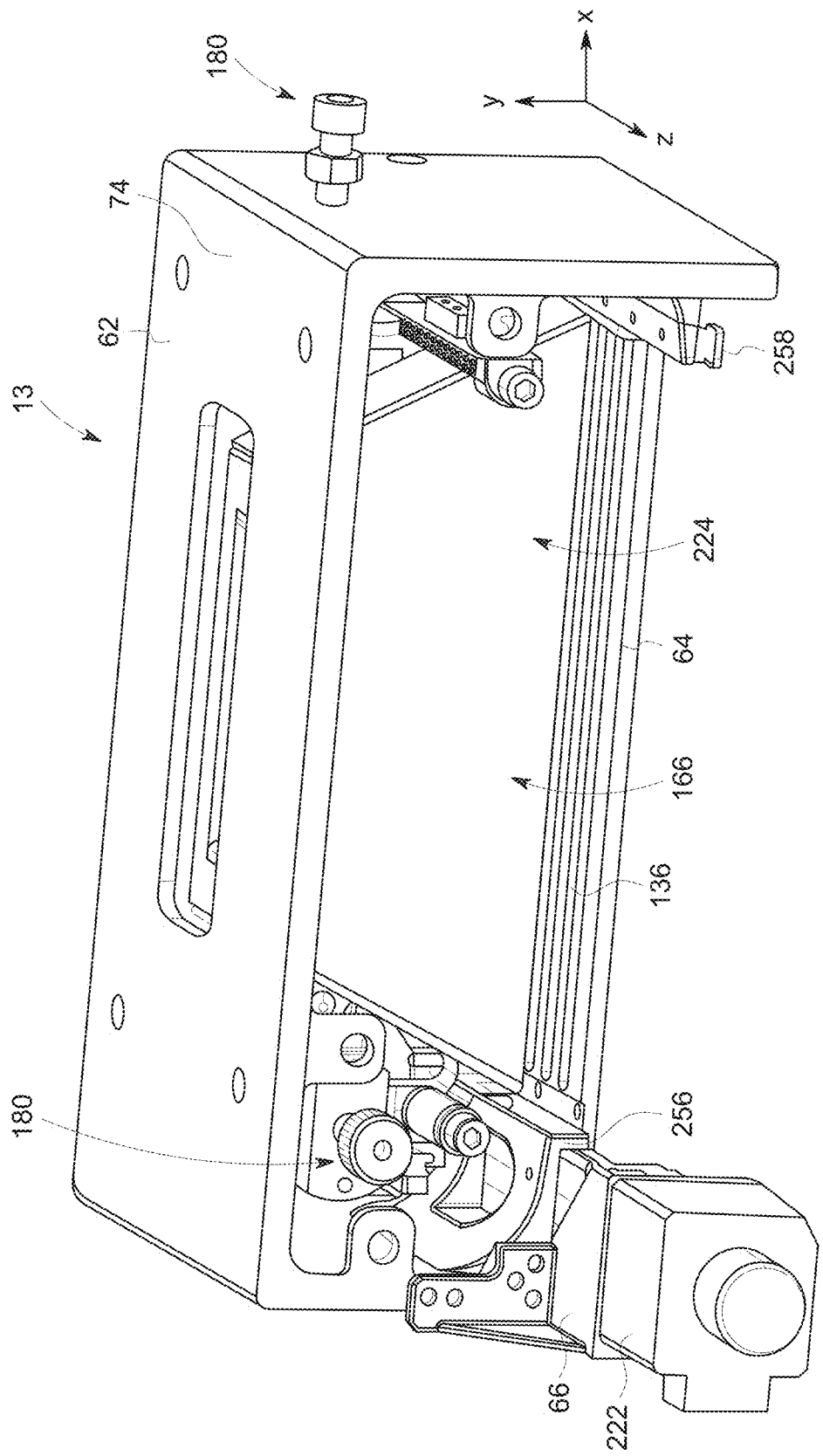
FIG. 31 is a perspective view of an assembled pre-patient collimator, in accordance with aspects of the present disclosure.

FIG. 31 is a perspective view of an assembled pre-patient collimator 13. The collimator 13 includes the additively manufactured collimator housing 62, the additively manufactured aperture carrier plate 64, and the additively manufactured motor mounting plate 66 described above with a few alterations. For example, the aperture carrier plate 64 lacks mounting brackets. The plate portion 136 of the aperture carrier plate 64 is coupled (e.g., indirectly via guides rails and actuators) to the integral side structures 256, 258 of the collimator housing 62. The side structures 256, 258 are located further away from the first wall 74 compared to similar side structures in the collimator housing 62 of FIGS. 7-10. In addition, the collimator 13 includes the in-built alignment mechanism 224, the adjustment mechanism 180, and a motor 222 coupled to the motor mounting plate 66 and configured to move the aperture carrier plate 64 (via actuators and rail guides).

Figure 32:
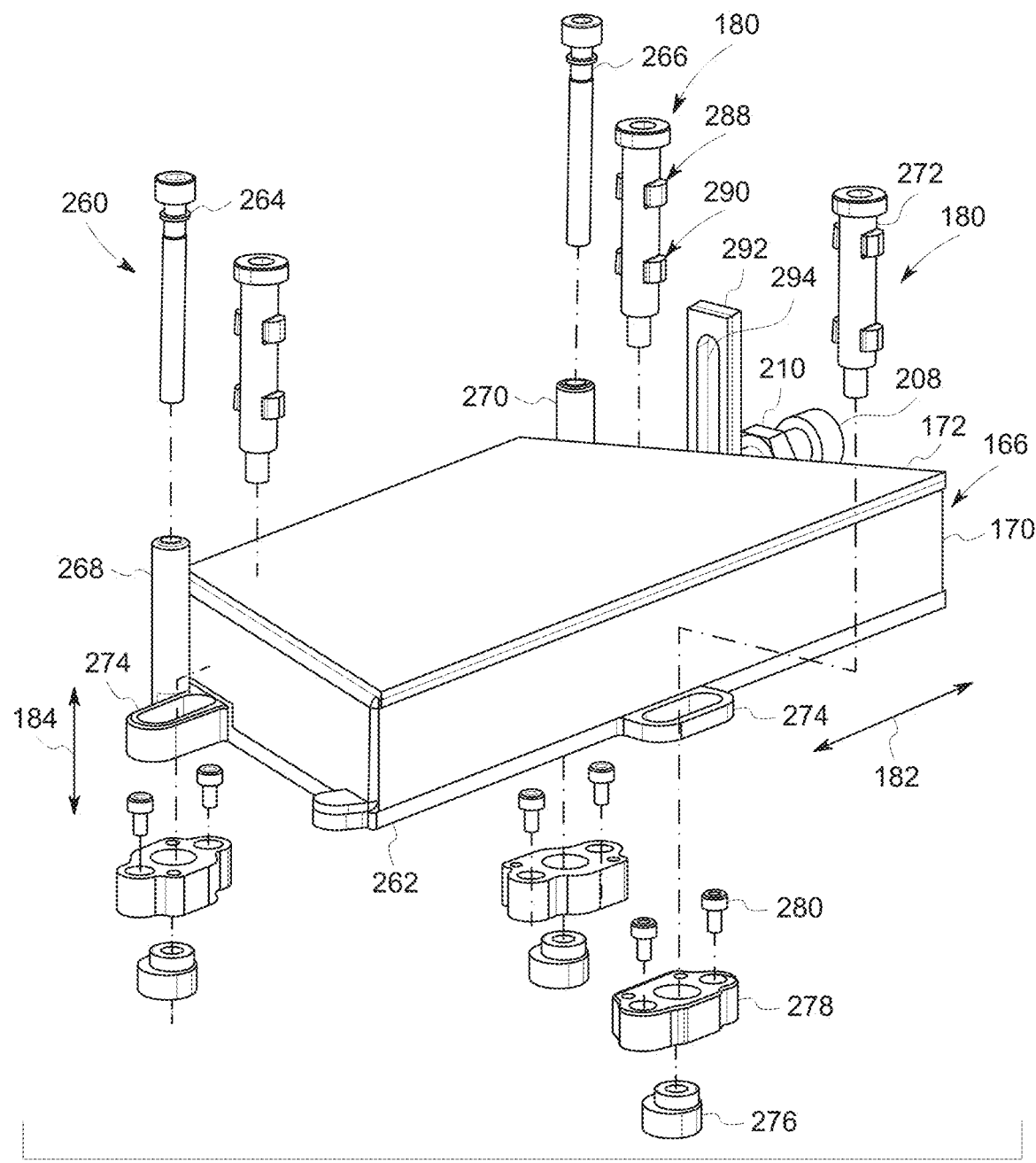
FIG. 32 is an exploded view of another in-built alignment mechanism for moving a bowtie filter assembly within a collimator housing, in accordance with aspects of the present disclosure.

FIG. 32 is an exploded view of another in-built alignment mechanism 260 for moving the bowtie filter assembly 166 within a collimator housing. The bowtie filter assembly 166 includes a base plate or filter mounting plate 262, a bowtie filter 170 (e.g., made of polytetrafluoroethylene), and a cover 172 (e.g., front cover). The filter mounting plate 262 and the cover 172 partially enclose the bowtie filter 170 within. The cover 172 does not extend around a top and bottom portion of the bowtie filter 170. In certain embodiments, a radiation shielding layer (e.g., made of a tungsten-based polymer) is disposed on the surface of the filter mounting plate 262 that directly interfaces with the bowtie filter 170. In certain embodiments, a radiation shielding layer is disposed on the surfaces of the cover 172 that directly interface with the bowtie filter 170. The filter mounting plate 262 and the cover 172 are configured to house different types of bowtie filters 170. The bowtie filter 170 is coupled to or mounted to the filter mounting plate 262 via fasteners 178 (e.g., screws) that pass through corresponding openings on the bowtie filter 170 and the filter mounting plate 228. The cover 172 is coupled to or mounted to the filter mounting plate 262 to enclose the bowtie filter 170 via fasteners (not shown, e.g., screws) that pass through corresponding openings on the cover 172 and the filter mounting plate 262.

The in-built alignment mechanism 260 includes an adjustment mechanism 180 configured to move the bowtie filter assembly 166 in a first direction 182 (e.g., lateral direction) and a second direction 184 (e.g., transverse direction). The movement in the lateral direction 182 is independent of movement in the transverse direction 184. The movement in the lateral direction 182 occurs between the second wall 76 and the third wall 78 of the collimator housing 62 in FIGS. 7-10. The movement in the transverse direction 184 occurs toward and away from the fourth wall 80 of the collimator housing 62 in FIGS. 7-10. The lateral direction 182 is orthogonal to the transverse direction 184.

The in-built alignment mechanism 260 includes guides 264, 266 for the bowtie filter assembly 166 to move along. The guides 264, 266 are coupled to extensions 268, 270 that are a part of the filter mounting plate 262 and extend in the transverse direction 184 (e.g., away from the fourth wall 80 in FIGS. 7-10). The guides 264, 266 support the bowtie filter assembly 166. The guides 264, 266 extend through the receptacles 116 on the first wall 74 of the collimator housing 62 in FIGS. 7-10.

Figure 33:
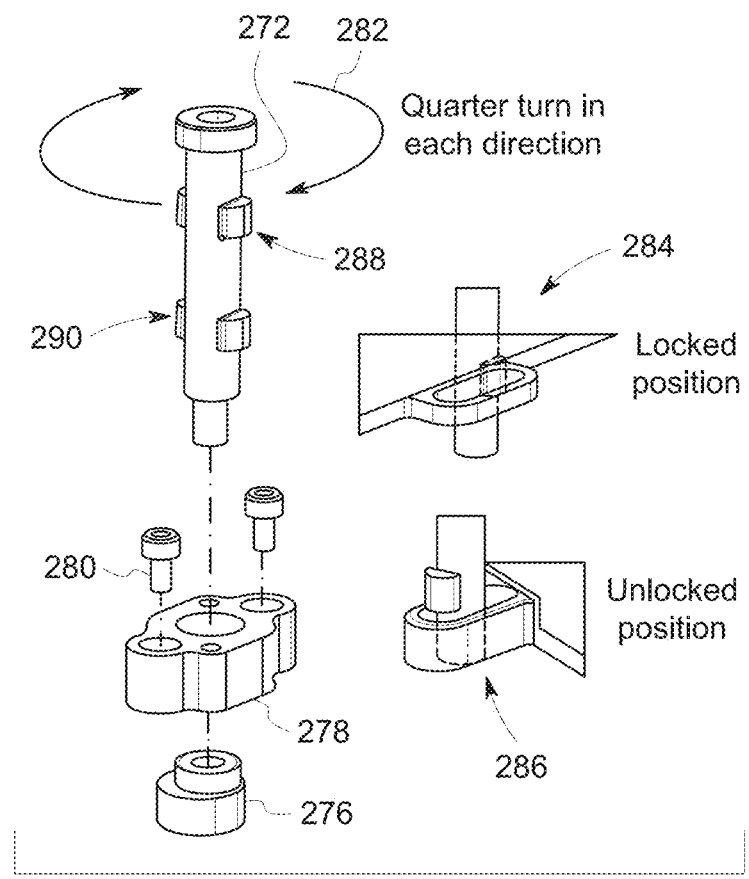
FIG. 33 is a schematic view of manipulating a guide pin of the in-built alignment mechanism of FIG. 32 between a locked position and an unlocked position, in accordance with aspects of the present disclosure.

The adjustment mechanism 180 includes 3 guide pins 272 that extend through respective receptacles 274 of the filter mounting plate 262 and into respective quarter turn bushes 276 (e.g., made of wear resistant material) disposed within support pads 278. The support pads 278 are coupled to the fourth wall 80 of the collimator housing 62 in FIGS. 7-10 via fasteners 280. The receptacles 274 enable movement of the bowtie filter assembly 166 in both the lateral direction 182 and the transverse direction 184. As depicted in FIG. 33, the guide pins 272 are configured to be rotated a quarter turn in either direction as indicated by arrows 280 between a locked position 284 and an unlocked position 286. Each guide pin 272 includes a first set of projections 288 and a second set of projections 290 at different axial locations along the respective guide pin 272. The first set of projections 288 and the second set of projections 290 form two different axial locations for the bowtie filter assembly 166 to be moved in the transverse direction 184 (one position with the bowtie filter 170 in the scan plane and one position with the bowtie filter 172 outside of the scan plane). In the unlocked position, the first set of projections 288 and/or the second set of projections 290 pass through the receptacles 274 enabling movement of the bowtie filter assembly 166 in the transverse direction 184. In the locked position, either the first set of projections 288 or the second set of projections 290 interface with the wall defining the receptacles 274 to block movement of the bowtie filter assembly 166 in the transverse direction 184.

The adjustment mechanism 180 includes a frame 292 that is part of and extends from the filter mounting plate 262. The frame 292 enables motion of the bowtie filter assembly 166 in the lateral direction 182 which is independent of the movement in the transverse direction 184. The frame 292 extends in the direction 184 parallel with the second wall 76 and the third wall 78 of the collimator housing 162 in FIGS. 7-10. The frame 292 includes a slot 294.

The adjustment mechanism 180 includes an adjustment screw 208 that adjusts movement of the bowtie filter assembly 166 in the lateral direction 182 within the collimator housing 62 of FIGS. 7-10. The adjustment screw 208 enables adjusting the bowtie filter assembly 166 so that the bowtie filter 170 is in the isocenter of the X-ray beam. A portion of the adjustment screw 208 extends through a nut 210 (e.g., lock nut) on the outside of the collimator housing 62 and into the interior space 110 (via an opening in the second wall 76) of the collimator housing 62. Within the collimator housing 62, the portion of the adjustment screw 208 extends through the slot 294 and secured via a fastener 212 (e.g., nut) to the frame 292. Rotation of the adjustment screw 208 moves the bowtie filter assembly 166 in the lateral direction 182. Each end of the slot 294 acts as a limit on movement of the bowtie filter assembly 166 in the transverse direction 184. Once adjustment is complete, the lock nut 210 may be utilized to freeze the position of the bowtie filter assembly 166. The actuation of the adjustment screw 208 may be done mechanically. In certain embodiments, the actuation of the adjustment screw 208 may occur automatically via a motorized actuator (in response to a control signal from processing circuitry of the collimator controller 29 in FIG. 1) coupled to the adjustment screw 208. Rotation of the adjustment screw 208 in a circumferential direction towards the fourth wall 80 results in movement of the bowtie filter assembly 166 in the lateral direction 182 towards the second wall 76 of the collimator housing 62 in FIGS. 7-10 while rotation of the adjustment screw 208 in the circumferential direction away from the fourth wall 80 results in movement of the bowtie filter assembly 166 in the lateral direction 182 towards the third wall 78.

Figure 34:
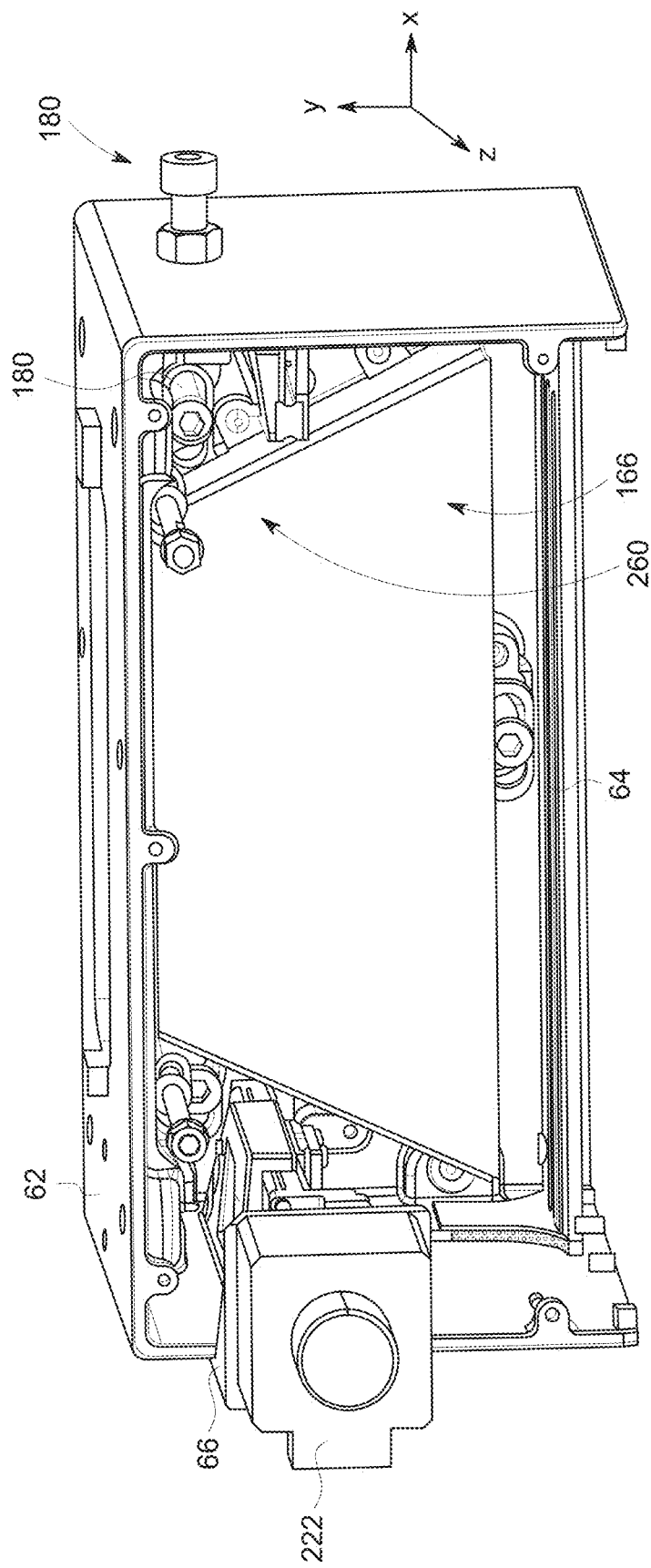
FIG. 34 is a perspective view of an assembled pre-patient collimator, in accordance with aspects of the present disclosure.

FIG. 34 is a perspective view of an assembled pre-patient collimator 13. The collimator 13 includes the additively manufactured collimator housing 62, the additively manufactured aperture carrier plate 64, and the additively manufactured motor mounting plate 66 described above. In addition, the collimator 13 includes the in-built alignment mechanism 260, the adjustment mechanism 180, and a motor 222 coupled to the motor mounting plate 66 and configured to move the aperture carrier plate 64 (via actuators and rail guides).

Figure 35:
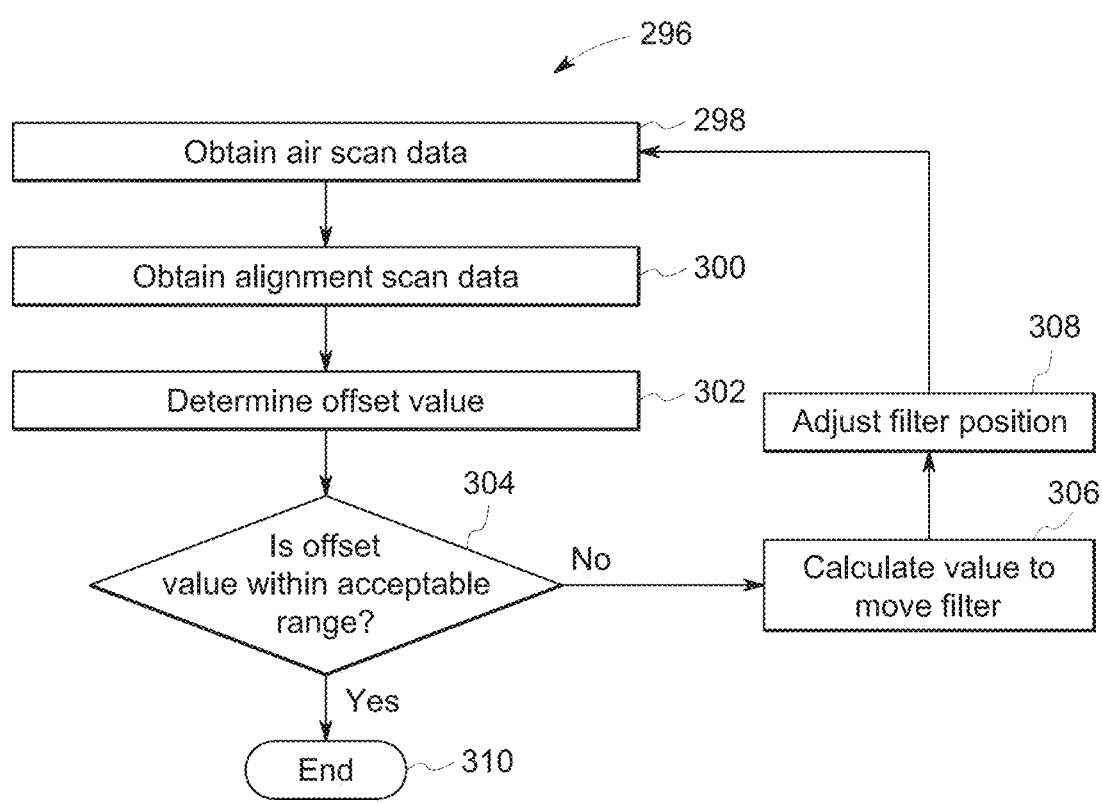
FIG. 35 is a flow chart of a method for centering a bowtie filter, in accordance with aspects of the present disclosure.

FIG. 35 is a flow chart of a method 296 for centering a bowtie filter with respect to an X-ray beam center. The method 296 may be performed utilizing one or more components of the CT system 10 (e.g., computer 36, collimator controller 29, etc.) in FIG. 1. The method 296 includes obtaining air scan data with a bowtie filter (e.g., as part of the bowtie filter assembly) within a pre-patient collimator moved out of view or out of a scan plane prior to the air scan (block 298). The bowtie filter may be moved out of the scan plane utilizing one of the adjustment mechanisms described above for moving the bowtie filter assembly in the transverse direction. The bowtie filter is not removed from the collimator during block 298. The method 296 also includes obtaining alignment scan data (e.g., via a center body filter scan) after the bowtie filter has been moved in the transverse direction into the scan plane (via the same adjustment mechanism) (block 300). The method 296 further includes calculating or determining (e.g., via processing circuitry) an offset value or distance from a center of a beam line path based on the air scan data and the alignment scan data (block 302). The method 296 still further include comparing the offset value to an acceptable range or desired range for a center position of the bowtie filter (e.g., where the center of the bowtie filter is coincident with the isocenter alignment) (block 304). If the offset value is outside the acceptable range, the method 296 includes calculating (e.g., via processing circuitry) a value or distance to move the bowtie filter in the lateral direction to achieve a desired center position (e.g., within the acceptable range) (block 306). The method 296 yet further includes moving the bowtie filter the calculated value or distance (e.g., in a fraction of millimeters) in the lateral direction utilizing one of the adjustment mechanisms described above (e.g., adjustment screw 208) (block 308). The adjustment of the bowtie filter in the lateral direction may occur automatically based on a control signal (e.g., from the collimator controller 29) to an actuator coupled to the adjustment mechanism (e.g., adjustment screw 208) for moving the bowtie filter in the lateral direction. The method 296 then repeats blocks 298-304. If the offset value is within the acceptable range, the method 296 ends (block 310).

Technical effects of the disclosed embodiments include providing an in-built alignment mechanism disposed within a pre-patient collimator for precise and easy adjustments of the collimator during system alignment. In particular, the in-built alignment mechanism enables a bowtie filter to be adjusted (e.g., to be centered with respect to an X-ray beam path to provide very good image quality) in a both a lateral direction and a transverse direction independent of each other. The configuration of the in-built alignment mechanism also enables adjustments (e.g., via an actuator mechanism) of the bowtie filer to occur from outside a collimator housing without having to remove or disassemble a subcomponent (e.g., bowtie filter) from the collimator during the system alignment. In addition, the in-built alignment mechanism is configured to be utilized with different types of bowtie filters and is scalable to be utilized with different imaging platforms.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A pre-patient collimator for a computed tomography (CT) imaging system, comprising:
a collimator housing comprising a plurality of walls, wherein the plurality of walls comprises a first wall configured to face an X-ray source when the pre-patient collimator is coupled to the CT imaging system, and the plurality of walls comprises a second wall and a third wall flanking the first wall;
a bowtie filter assembly disposed within the collimator housing and comprising a bowtie filter, wherein the bowtie filter assembly comprises a filter mounting plate and a cover for partially enclosing the bow tie filter within the bowtie filter assembly; and
an adjustment mechanism configured to move the bowtie filter assembly in a lateral direction between the second wall and the third wall within the collimator housing.

2. The pre-patient collimator of claim 1, wherein the plurality of walls comprises a fourth wall extending between the second wall and the third wall adjacent the first wall, and the adjustment mechanism is configured to move the bowtie filter assembly in a transverse direction toward and away from the fourth wall.

3. The pre-patient collimator of claim 1, comprising a motorized actuator coupled to the adjustment mechanism and the motorized actuator is configured, in response to a control signal from a processor, to actuate the adjustment mechanism to move the bowtie filter assembly in the lateral direction to center the bowtie filter with an X-ray beam emitted by the X-ray source.

4. The pre-patient collimator of claim 1, wherein respective surfaces of both the filter mounting plate and the cover facing the bowtie filter have radiation shielding material disposed on them.

5. The pre-patient collimator of claim 1, wherein the filter mounting plate and cover are configured to partially enclose different types of bowtie filters within them.

6. The pre-patient collimator of claim 2, wherein movement of the bowtie filter assembly in the lateral direction is independent of movement of the bowtie filter assembly in the transverse direction.

7. The pre-patient collimator of claim 2, wherein the adjustment mechanism is configured to be manipulated from outside the collimator housing to move the bowtie filter assembly in the lateral direction and the transverse direction within the collimator housing.

8. The pre-patient collimator of claim 6, wherein the adjustment mechanism comprises a frame disposed within the collimator housing and coupled to the bowtie filter assembly, an adjustment screw coupled to the frame and configured to adjust movement of the bowtie filter assembly in the lateral direction, and a lock pin coupled to the frame and configured to adjust movement of the bowtie filter assembly in the transverse direction.

9. The pre-patient collimator of claim 8, wherein the frame comprises a first opening for receiving the lock pin when the bowtie filter assembly is moved in the transverse direction out of a scan plane and a second opening for receiving the lock pin when the bowtie filter assembly is moved in the transverse direction into the scan plane.

10. The pre-patient collimator of claim 9, wherein the frame comprises a slot that the adjustment screw extends through, wherein the slot is configured to keep the adjustment screw extending through the slot as the bowtie filter assembly is moved in the lateral direction.

11. A pre-patient collimator for a computed tomography (CT) imaging system, comprising:
a collimator housing;
a bowtie filter assembly disposed within the collimator housing and comprising a bowtie filter; and
an adjustment mechanism configured to move the bowtie filter assembly in a first direction and a second direction within the collimator housing, wherein a movement of the bowtie filter assembly in the first direction is independent of a movement of the bowtie filter assembly in the second direction, and wherein the first direction and the second direction are orthogonal to each other, and wherein the adjustment mechanism is configured to be manipulated from outside the collimator housing to move the bowtie filter assembly in the first direction and the second direction within the collimator housing.

12. The pre-patient collimator of claim 11, wherein the collimator housing comprises a first wall configured to face an X-ray source when the pre-patient collimator is coupled to the CT imaging system, and wherein the first direction and the second direction are orthogonal to each other along a plane that is parallel within the first wall.

13. The pre-patient collimator of claim 11, wherein the collimator housing comprises a plurality of walls, wherein the plurality of walls comprises a first wall configured to face an X-ray source when the pre-patient collimator is coupled to the CT imaging system, and the plurality of walls comprises a second wall and a third wall flanking the first wall, and wherein the adjustment mechanism is configured to move the bowtie filter assembly in the first direction between the second wall and the third wall.

14. The pre-patient collimator of claim 11, wherein the bowtie filter assembly comprises a filter mounting plate and a cover for partially enclosing the bow tie filter within the bowtie filter assembly.

15. The pre-patient collimator of claim 11, wherein the adjustment mechanism comprises a frame disposed within the collimator housing and coupled to the bowtie filter assembly, an adjustment screw coupled to the frame and configured to adjust movement of the bowtie filter assembly in the first direction, and a lock pin coupled to the frame and configured to adjust movement of the bowtie filter assembly in the second direction.

16. The pre-patient collimator of claim 13, wherein the plurality of walls comprises a fourth wall extending between the second wall and the third wall adjacent the first wall, and the adjustment mechanism is configured to move the bowtie filter assembly in the second direction toward and away from the fourth wall.

17. A method for performing collimator bowtie filter centering, comprising:
obtaining, at a processor, air scan data acquired via an air scan utilizing a computed tomography (CT) imaging system with a bowtie filter moved out of view of an X-ray beam emitted by an X-ray source of the CT imaging system prior to an air scan to obtain the air scan data, wherein the bowtie filter is disposed within a bowtie filter assembly disposed within a collimator housing, and wherein the bowtie filter assembly is configured to be moved in a first direction and a second direction within the collimator housing, the first direction being orthogonal to the second direction;
obtaining, at the processor, alignment data acquired via an air scan utilizing the CT imaging system with the bowtie filter moved in the second direction to within the scan plane prior to an alignment scan to obtain the air scan data;

calculating, via the processor, an offset distance of the bowtie filter from a beam line path of the X-ray beam;

comparing, via the processor, the offset distance to an acceptable range for a desired center position of the bowtie filter within the X-ray beam;

calculating, via the processor, a distance to move the bowtie filter in the second direction to center the bowtie filter within the X-ray beam when the offset distance is outside the acceptable range; and moving, in response to a control signal from the processor, the bowtie filter in the second direction by the distance.

18. The method of claim 17, wherein movement of the bowtie filter assembly in the first direction is independent of movement of the bowtie filter assembly in the second direction.

* * * * *